(12) United States Patent
Winter et al.

(10) Patent No.: US 12,285,494 B2
(45) Date of Patent: Apr. 29, 2025

(54) METHODS FOR TREATING B-ALL BY ADMINISTERING A PRE-BCR COMPLEX ANTAGONIST

(71) Applicant: Children's Health Care, Minneapolis, MN (US)

(72) Inventors: Stuart Sheldon Winter, Albuquerque, NM (US); Bridget Smith Wilson, Albuquerque, NM (US)

(73) Assignee: Children's Health Care, Minneapolis, MN (US)

( * ) Notice: Subject to any disclaimer, the term of this patent is extended or adjusted under 35 U.S.C. 154(b) by 24 days.

(21) Appl. No.: 17/672,573

(22) Filed: Feb. 15, 2022

(65) Prior Publication Data

US 2022/0265846 A1    Aug. 25, 2022

Related U.S. Application Data

(60) Provisional application No. 63/149,728, filed on Feb. 16, 2021, provisional application No. 63/278,030, filed on Nov. 10, 2021.

(51) Int. Cl.
*A61K 47/68* (2017.01)
*A61K 31/704* (2006.01)
*A61P 35/02* (2006.01)

(52) U.S. Cl.
CPC ........ *A61K 47/6849* (2017.08); *A61K 31/704* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 5,182,205 A | 1/1993 | Bauer et al. | |
| 6,335,157 B1 | 1/2002 | Gonzalez et al. | |
| 6,335,175 B1* | 1/2002 | Tsuganezawa ... | G01N 33/56972 530/389.1 |
| 10,858,448 B2* | 12/2020 | Horowitz ............... | C07K 16/42 |
| 10,988,533 B2 | 4/2021 | Wilson et al. | |
| 2003/0215453 A1* | 11/2003 | Dedera ............ | G01N 33/57492 435/6.16 |
| 2006/0257397 A1 | 11/2006 | Throsby et al. | |
| 2010/0062950 A1 | 3/2010 | Bhatt et al. | |
| 2011/0262440 A1 | 10/2011 | Zugmaier | |
| 2012/0201756 A1 | 8/2012 | Sexton | |
| 2014/0228544 A1 | 8/2014 | Bhatt et al. | |
| 2016/0009813 A1 | 1/2016 | Themeli et al. | |
| 2018/0265594 A1* | 9/2018 | Horowitz ............... | C07K 16/18 |
| 2022/0265821 A1* | 8/2022 | Gray ...................... | A61P 35/02 |

FOREIGN PATENT DOCUMENTS

| | | |
|---|---|---|
| AU | 2003213064 A1 | 9/2003 |
| CN | 102498210 | 6/2012 |
| EP | 269127 | 6/1988 |
| JP | H1142087 | 2/1999 |
| JP | 11-133028 A | 5/1999 |
| KR | 1020120095343 A | 8/2012 |
| WO | 2004/106381 | 12/2004 |
| WO | 2008/118970 | 10/2008 |
| WO | 2010/006286 | 1/2010 |
| WO | 2016/127043 | 8/2016 |
| WO | 2016126488 A1 | 8/2016 |
| WO | 2018102795 A2 | 6/2018 |
| WO | 2021021846 A1 | 2/2021 |

OTHER PUBLICATIONS

Lloyd et al., Protein Engineering, Design & Selection 22:159-168 (Year: 2009).*
Edwards et al., J Mol Biol 334(1): 103-118 (Year: 2003).*
Strop et al., Chemistry and Biology 20: 161-167 (Year: 2013).*
Donaghy et al., mAbs 8:659 (Year: 2016).*
Hamann et al., Bioconjugate Chem 16: 346-353 (Year: 2005).*
"Rare Pediatric Disease (RPD) Designation and Voucher Programs", (2021), Retrieved Jun. 26, 2021 from https://www.fda.gov/industry/developing-products-rare-diseases-conditions/rare-pediatric-disease-rpd-designation-and-voucher-programs, 2 pages.
Erasmus, et al., "Dynamic pre-BCR homodimers fine-tune autonomous survival signals in B cell precursor acute lymphoblastic leukemia", Science Signaling, 9 ra116, (2016):1-17.
Hills, Bethany, (2020) "Bill Proposes Continuation of FDA Rare Pediatric Disease Priority Review Vouchers", JD Supra, Retrieved Jun. 26, 2021, from https://www.jdsupra.com/legalnews/bill-proposes-continuation-of-fda-rare-81623/, 4 pages.
Inaba, Hiroto et al., "Pediatric acute lymphoblastic leukemia", Haematologica. Nov. 1, 2020;105(11):2524-2539.
Inserro, Allison, "NCCN Releases Clinical Practice Guidelines for Pediatric ALL", Retrieved Jun. 21, 2021, from: https://www.ajmc.com/view/nccn-releases-clinical-practice-guidelines-for-pediatric-all, published May 30, 2019, 2 pages.
Karst, Kurt R., "Pediatric Exclusivity: Amazingly Powerful, Essentially Ironclad . . . and Often Overlooked", Jul. 7, 2015, located online at: http://www.fdalawblog.net/2015/07/pediatric-exclusivity-amazingly-powerful-essentially-ironclad-and-often-overlooked/, 3 pages.
Kohrer, S. et al., "Pre-BCR signaling in precursor B-cell acute lymphoblastic leukemia regulates PI3/AKT, FOXO1 and MYC, and can be targeted by SYK inhibition", Leukemia (2016) 30(6):1246-1254.
Leukemia and Lymphoma Society, "ALL Subtypes", (2021), Retrieved Jun. 25, 2021, from https://www.lls.org/leukemia/acute-lymphoblastic-leukemia/diagnosis/all-subtypes, 2 pages.

(Continued)

*Primary Examiner* — Phuong Huynh
(74) *Attorney, Agent, or Firm* — Merchant & Gould P.C.

(57) ABSTRACT

Methods and compositions for treating B-cell acute lymphoblastic leukemia (B-ALL) in a pediatric subject are provided. The methods comprise administering to the subject one or more doses of an antibody-drug conjugate, wherein the antibody or antigen-binding fragment thereof specifically binds CD179a.

13 Claims, 19 Drawing Sheets

Specification includes a Sequence Listing.

(56) References Cited

OTHER PUBLICATIONS

Nejadmoghaddam, et al., "Antibody-Drug Conjugates: Possibilities and Challenges", Avicenna J Med Biotechnol, 2019;11(1):3-23.
PDQ® Pediatric Treatment Editorial Board, "PDQ Childhood Acute Lymphoblastic Leukemia Treatment", Bethesda, MD: NIH National Cancer Institute, Updated Jun. 4, 2021, Available at: https://www.cancer.gov/types/leukemia/hp/child-all-treatment-pdq. [Accessed Jun. 21, 2021]. [PMID: 26389206], 181 pages.
Reth, Michael et al., "Signaling Circuits in Early B-Cell Development", 2014, Advances in Immunology, vol. 122: 129-75.
Williams, Sherry et al., "Inotuzumab Ozogamicin in Relapsed or Refractory B-Cell Acute Lymphoblastic Leukemia", J Adv Pract Oncol. 2018;9(6):670-676.
Winkler, Thomas et al., "The Role of the Pre-B Cell Receptor in B Cell Development, Repertoire Selection, and Tolerance", Frontiers in Immunology, Nov. 15, 2018;9:2423, 10 pages.
Winter, Stuart et al., "VpreB surrogate light chain expression in B-lineage ALL: a report from the Children's Oncology Group", Jan. 25, 2022, Blood Advances, 6(2):585-589.
NCCN Clinical Practice Guidelines in Oncology, "Pediatric Acute Lymphoblastic Leukemia", Version 1.2022, Oct. 1, 2021, located at: https://www.nccn.org/professionals/physician_gls/pdf/ped_all.pdf, 122 pages.
Muschen, Markus, "Rationale for targeting the pre-B-cell receptor signaling pathway in acute lymphoblastic leukemia", Blood, Jun. 11, 2015, vol. 125, No. 24, 3688-3693.
Chen, Dongfeng et al., "The Expression Pattern of the Pre-B Cell Receptor Components Correlates with the Cellular Stage and Clinical Outcome in Acute Lymphoblastic Leukemia", PLOS ONE, DOI: 10.1371/journal.pone.0162638, Sep. 9, 2016, 16 pages.
Arlotta, Keith, "In-Depth Comparison of Lysine-Based Antibody-Drug Conjugates Prepared on Solid Support Versus in Solution", Antibodies 2018, 7, 6, doi:10.3390/antib7010006, www.mdpi.com/journal/antibodies, 17 pages.
Cao, Mingyan et al., "Site-specific antibody-drug conjugate heterogeneity characterization and heterogeneity root cause analysis", MABS 2019, vol. 11, No. 6, 1064-1076.
Geng et al., "Self-Enforcing Feedback Activation between BCL6 and Pre-B Cell Receptor Signaling Defines a Distinct Subtype of Acute Lymphoblastic Leukemia", 2015, Cancer Cell 27, 409-425.
Andrews et al., "Actin restricts FceRI diffusion and facilitates antigen-induced receptor immobilization," Nat Cell Biology, Aug. 2008; 10:955-963.
Andrews et al., "Small, Mobile FceRI Receptor Aggregates are Signaling Competent," Immunity, Sep. 18, 2009; 31:469-479.
Asner et al., "Obesity in Long-Term Survivors of Childhood Acute Lymphoblastic Leukemia," Pediatric Blood Cancer, 2008; 51:118-122.
Babor et al., "Invasive Aspergillosis in Pediatric Oncology Patients: A Rare Event with Poor Prognosis—Case Analysis to Plan Better Targeted Prophylactic or Therapeutic Measurement," Klin Pediatr, 2012; 224:160-165.
Bankovich et al., "Structural Insight into Pre-B Cell Receptor Function," Science, Apr. 13, 2007; 316:291-294.
Barondes et al., "Structure and Function of a Large Family of Animal Lectins," The Journal of Biological Chemistry, Aug. 19, 1994; 269(33):20807-20810.
Bologa et al. "Compound Collection Preparation for Virtual Screening," Methods in Molecular Biology, 2012; 910:125-143.
Bradbury et al., "Beyond natural antibodies: the power of in vitro display technologies," Nature Biotechnology, Mar. 2011; vol. 29(3):245-254.
Cardo-Vila et al., "From combinatorial peptide selection to drug prototype (II): Targeting the epidermal growth factor receptor pathway," PNAS, Mar. 16, 2010; 107(11): 5118-5123.
Carroll-Portillo et al., "Formation of a Mast Cell Synapse: FceRI Membrane Dynamics upon Binding Mobile or Immobilized Ligands on Surfaces," J of Immunology, 2010; 184: 1328-1338.
Collins, et al., "A genome annotation-driven approach to cloning the human ORFeome." Genome Biol. (2004); 5(10):R84.
Cutler et al., "Multi-Color Quantum Dot Tracking Using a High-Speed Hyperspectral Line-Scanning Microscope," Plos One, May 2013; 8(5): e64320.
Davis et al., "Chronic active B-cell-receptor signaling in diffuse large B-cell lymphoma," Nature, Jan. 7, 2010; 463:88-92.
Douer, "Adult Acute Lymphoblastic Leukemia: A Cancer with No. Standard of Care," Acta Haematol, Apr. 2013; 130:196-198.
Elantak et al., "Structural Basis for Galectin-1-dependent Pre-B cell Receptor (Pre-BCR) Activation," The Journal of Biological Chemistry, 2012; 287(53):44703-44713.
Eswar et al., "Comparative Protein Structure Modeling Using Modeler," Curr Protoc Bioinformatics, Oct. 2006, Unit-5.6, 47 pages.
European Extended Search Report for EP Application No. 16747000.4//PCT/US2016/015166 dated Oct. 16, 2018, 25 pages.
European Extended Search Report No. EP 16747327.1/PCT/US2016/016753, dated Aug. 29, 2018; 8 pages.
Ferrara et al., "Using Phage and Yeast Display to Select Hundreds of Monoclonal Antibodies: Application to Antigen 85, a Tuberculosis Biomarker," Plos One, Nov. 2012; 7(11): e49535.
Gauthier et al., "Galectin-1 is a stromal cell ligand of the pre-B cell receptor (BCR) implicated in synapse formation between pre-B and stromal cells and in pre-BCR triggering," PNAS, Oct. 1, 2002; 99(20): 13014-13019.
Gaynon et al., "Long-term Results of the Children's Cancer Group Studies for Childhood Acute Lymphoblastic Leukemia 1983-2002: a Children's Oncology Group Report," Leukemia, Feb. 2010; 24(2):285-297.
Giordano et al., "Galectins in hematological malignancies" Current Opinion in Hematology, 2013; 20:327-335.
Goennenwein et al., "Functional Incorporation of Integrins into Solid Supported Membranes on Ultrathin Films of Cellulose: Impact on Adhesion," Biophysical Journal, Jul. 2003; 85:646-655.
Harvey et al., "Identification of novel cluster groups in pediatric high-risk B-precursor acute lymphoblastic leukemia with gene expression profiling: correlation with genome-wide DNA copy number alterations, clinical characteristics, and outcome," Blood, Dec. 2, 2010; vol. 116(23): 4874-4884.
Hauser et al., "Calmodulin inhibition of E2A stops expression of surrogate light chains of the pre-B-cell receptor and CD19," Molecular Immunology (2010); 47(5): 1031-1038.
Hollis, et al., "Immunoglobulin A light-chain-related genes 14.1 and 16.1 are expressed in pre-B cells and may encode the human immunoglobulin m light-chain protein." Proc Natl Acad Sci USA, (1989); 86(14): 5552-5556.
Hunger et al., "Childhood Leukemia—New Advances and Challenges," New England J of Medicine, Aug. 5, 2004; 351(6): 601-603.
Hunger et al., "Improving Outcomes for High-Risk ALL: Translating New Discoveries Into Clinical Care" Pediatric Blood & Cancer, 2011; vol. 56:984-993.
Karasuyama et al., "A complex of glycoproteins is associated with V-preB/larnbda-5 surrogate light chain on the surface of mu heavy chain-negative early precursor B cell lines," Journal of Experimental Medicine (1993); 178(2): 469-478.
Karasuyama, et al., "Surrogate light chain in B cell Development." Advances in Immunology, (1996); 63: 1-41.
Kepley et al., "Negative regulation of FceRI signaling by FcγRII costimulation in human blood basophils" J Allergy Clinical Immunology, 2000; 106(2):337-348.
Kim et al., "Independent Trafficking of Ig-α/Ig-β and μ-Heavy Chain Is Facilitated by Dissociation of the B Cell Antigen Receptor Complex," J Immunology, 2005; 175:147-154.
Kitamura, et al., "A critical role of A 5 protein in B cell development." Cell (1992); 69(5):823-831.
Kiyokawa Nobutaka et al., "Diagnostic importance of CD179a/b as markers of precursor B-cell lymphoblastic lymphoma," Modern Patho. (2004); 17(4): 423-429.
Lemmers et al. "The Human (1/JL+μ-) proB Complex: Cell Surface Expression and Biochemical Structure of a Putative Transducing Receptor," Blood, Jun. 15, 1999; 93(12):4336-4346.
Lidke et al., "Caught in the act: quantifying protein behavior in living cells," Trends in Cell Biology, 2004; 19(11):566-573.

(56) References Cited

OTHER PUBLICATIONS

Lidke et al., "Quantum dot ligands provide new insights into erB/HER receptor-mediated signal transduction" Nature Biotechnology, Feb. 2004; 22(2): 198-203.

Lillemeier et al., "Plasma membrane-associated proteins are clustered into islands attached to the cytoskeleton" PNAS, Dec. 12, 2006; 103(50):18992-18997.

Low-Nam et al., "ErbB1 dimerization is promoted by domain co-confinement and stabilized by ligand binding," Nature Structural & Molecular Biology, Nov. 2011; vol. 18(11):1244-1249.

Lund et al., "Risk Factors for Treatment Related Mortality in Childhood Acute Lymphoblastic Leukaemia," Pediatric Blood & Cancer, 2011; 56:551-559.

Matlawska-Wasowska et al., "Macrophage and NK-mediated Killing of Precursor-B Acute Lymphoblastic Leukemia Cells Targeted with a-Fucosylated Anti-CD19 Humanized Antibodies," Leukemia, Jun. 2013; 27(6): 1263-1274.

Meffre, et al., "Circulating human B cells that express surrogate light chains and edited receptors." Nature Immunology (2000); 207-213.

Melchers, et al., "Fit for life in the immune system? Surrogate L chain tests H chains that test L chains." Proc Natl Acad Sci U SA. (1999); 96(6): 2571-2573.

Melchers, et al., "The surrogate light chain in B-cell development," Immunology Today (1993);14(2):60-68.

Meng et al., "GSI-I (Z-LLNle-CHO) inhibits y-secretase and the proteasome trigger cell death in precursor-B acute lymphoblastic leukemia" Leukemia, 2011; 25:1135-1146.

Meng et al., "IKK inhibitor bay 11-7082 induces necroptotic cell death in precursor-B acute lymphoblastic leukaemic blasts" British J Haematology, 2010; 148:487-490.

Minegishi, et al., "Mutations in the human A5/14.I gene result in B cell deficiency and agammaglobulinemia." J Exp Med. (1998); 187 (1): 71-77.

Monroe, "ITAM-mediated tonic signaling through pre-BCR and BCR complexes," Nature Reviews. Immunology, Apr. 2006; 6:283-294.

Mourcin et al., "Galectin-1-expressing stromal cells constitute a specific niche for pre-Bll cell development in mouse bone marrow," Blood, Jun. 16, 2011; 117(24):6552-6561.

Mundt et al., "Only VpreB1, but not VpreB2, is expressed at levels which allow normal development of B cells," International Immunology (2006): 18 (1): 163-172.

Niemann et al., "B-cell receptor signaling as a driver of lymphoma development and evolution", Seminars in Cancer Biology, Dec. 2013; 23:410-421.

Ohnishi et al., "The nonimmunoglobulin portion of A5 mediates cell-autonomous pre-B cell receptor signaling," Nature Immunology, Sep. 2003; 4(9): 849-856.

Oliver et al., "Inhibition of Mast Cell FceR1-mediated Signaling and Effector Function by the Syk-selective Inhibitor, Piceatannol," The J of Biological Chemistry, Nov. 25, 1994; 269(47):29697-29703.

Oprea et al., "Drug repurposing from an academic perspective," Drug Discovery Today: Therapeutic Strategies, 2011; 8(3-4): 61-69.

Oprea et al., "Integrating virtual screening in lead discovery," Current Opinion in Chemical Biology, 2004; 8:349-358.

Owens, R.J. et al., "The Genetic Engineering of Monoclonal Antibodies", (1994) Journal of Immunological Methods, Feb. 1994, v. 168, pp. 149-165.

PCT International Preliminary Report on Patentability for International Application No. PCT/US2016/015166 dated Aug. 8, 2017, 6 pages.

PCT International Search Report and Written Opinion for International Application No. PCT/US2016/015166 dated Jul. 8, 2016, 10 pages.

PCT International Search Report and Written Opinion in Application PCT/US2016/016753, mailed May 26, 2016, 8 pgs.

PCT Notice of International Preliminary Report on Patentability: PCT/US2016/016753, mailed Aug. 17, 2017, 7 pgs.

Peluso et al., "Optimizing antibody immobilization strategies for the construction of protein microarrays," Analytical Biochemistry, 2003; 312: 113-124.

Rossi et al., "Clustering of Pre-B Cell Integrins Induces Galactin-1-Dependent Pre-B Cell Receptor Relocalization and Activation," Journal of Immunology, 2006; 177: 796-803.

Russell et al., "Differential Expression of Ikaros Isoforms in Monozygotic Twins With MLL-rearranged Precursor-B Acute Lymphoblastic Leukemia," Journal of Pediatric Hematology/Oncology, Dec. 2008; 30(12):941-944.

Safdari of al., "Antibody humanization methods—a review and update," 2013, Biotechnology and Genetic Engineering Reviews, vol. 29(2); pp. 175-186.

Shen et al., "Statistical potential for assessment and prediction of protein structures," Protein Science: a publication of the Protein Society, 2006; 15:2507-2524.

Steinkamp et al., "erbB3 Is an Active Tyrosine Kinase Capable of Homo- and Heterointeractions," Molecular and Cellular Biology, Mar. 2014; 34(6):965-977.

Stevenson et al., "B-cell receptor signaling in chronic lymphocytic leukemia," Blood, Oct. 20, 2011; 118(16):4313-4320.

Tovchigrechko et al., "GRAMM-X public web server for protein-protein docking," Nucleic Acids Research, 2006; 34:W310-314.

Tsourkas et al., "Discrimination of membrane antigen affinity by B Cells requires dominance of kinetic proofreading over serial engagement," Cellular & Molecular Immunology, 2012; 9:62-74.

UniProt Accession P12018, VPREB_HUMAN, Retrieved from the Internet on Jul. 2, 2024: https://www.ncbi.nlm.nih.gov/protein/P12018/, 5 pages.

UniProt Accession P15814, IGLL1_HUMAN, Retrieved from the Internet on Jul. 2, 2024: https://www.ncbi.nlm.nih.gov/protein/P15814/, 6 pages.

Van der Veer et al., "Interference with pre-B-cell receptor signaling offers a therapeutic option for TCF3-rearranged childhood acute lymphoblastic leukemia", Blood Cancer Journal 4, el81, pp. 1-4 (Year: 2014).

Wayne, "Application of Immunotherapy in Pediatric Leukemia," Current Hematologic Malignancy Reports, 2009; 4: 159-166.

Wells, "Geometric Simulation of Flexible Motion in Proteins", Methods in Molecular Biology, 2014; 1084; 173-192.

Wilson et al., "Spatio-Temporal Signaling in Mast Cells, "Methods in Molecular Biology, 2014; 1084:173-192, Advances Exp. Med Biol., 2011; 716:1-106.

Winnick et al., "Childhood Leukemia—New Advances and Challenges," The New England Journal of Medicine, Aug. 5, 2004; 351(6):601-603.

Winter et al., "High-Throughput Screening for Daunorubicin-Mediated Drug Resistance Identifies Mometasone Furoate as a Novel ABCB1-Reversal Agent," Journal of Biomolecular Screening, 2008; 13(3):185-193.

Winter et al., "Identification of genomic classifiers that distinguish induction failure in T-lineage acute lymphoblastic leukemia: a report from the Children's Oncology Group," Blood, Sep. 1, 2007; 110(5): 1429-1438.

Winter, "Pediatric Acute Leukemia Therapies Informed by Molecular Analysis of High-Risk Disease," American Society of Hematology, 2011; 366-373.

Xu, et al., "Combinatorial surrobody libraries." Proc. Natl. Acad Sci. USA (2008);105(31):10756-10761.

Xu, et al., "Surrobodies with Functional Tails." J Mol. Biol. (2010); 397(1): 352-360.

Yim et al., "The potential role of VPREB1 gene copy number variation in susceptibility to rheumatoid arthritis," Molecular Immunology (2010); 48(11): 1338-1343.

Gordon, Peter A. et al., "A Novel Antibody-Drug Conjugate Directed Towards the Surrogate Light Chain of Malignantly-transformed B-cell Precursors Reverses Leukemic Progression in NSG Mice", Blood (2022) 140 (Supplement), pp. 9201-9202.

Gordon et al., "A Novel Antibody-Drug Conjugate Directed Towards the Surrogate Light Chain of Malignantly-transformed B-cell Precursors Reverses Leukemic Progression in Mice", poster, Nov. 14, 2022, 1 page.

(56) References Cited

OTHER PUBLICATIONS

Epperly, Rebecca et al., "Long-term follow-up of CD19-CAR T-cell therapy in children and young adults with B-ALL", Hematology American Society of Hematology Educ Program, 2023, pp. 77-83.
Marcoux, Curtis et al., "Bone marrow necrosis and hyperinflammation after treatment with inotuzumab ozogamicin for B-cell acute lymphoblastic leukaemia", The Lancet, vol. 404, Issue 10459, Sep. 28, 2024, pp. 1253-1254.

* cited by examiner

```
┌─────────────────────────────────────────────────────────────┐
│       AALL0331 (n = 11 cases) & AALL0232 (n = 25 cases)     │
└─────────────────────────────────────────────────────────────┘
                    ↓                           ↓
┌───────────────────────────────┬───────────────────────────────┐
│    Day 0 Flow Evaluations     │    Day 28 Flow Evaluations    │
└───────────────────────────────┴───────────────────────────────┘
```

| 179a - PE (36) | 179a - FITC (21) | 179a - PE (16) | 179a - FITC (16) |
|---|---|---|---|
| PAPUNM | PARJSL | PARJSL | PARJSL |
| PARJSL | PANZGJ | PANZGJ | PANZGJ |
| PANTRP | PAPHLN | PAPHLN | PAPHLN |
| PAPKGP | PAPUDR | PAPUDR | PAPUDR |
| PANZGJ | PASZFV | PASZFV | PASZFV |
| PAPHLN | PARBXX | PARBXX | PARBXX |
| PAPUDR | PATEJI | PATEJI | PATEJI |
| PASZFV | PANEBL | PAPDNB | PAPDNB |
| PARBXX | PAPDNB | PAMYFJ | PAMYFJ |
| PAPVEG | PANPZS | PANRSR | PANRSR |
| PATEJI | PAMYFJ | PAPAJT | PAPAJT |
| PANEBL | PANRSR | PAPEXA | PAPEXA |
| PAPDNB | PAPAJT | PARCAH | PARCAH |
| PANPZS | PAPEXA | PATINT | PATINT |
| PARTCY | PARCAH | PAPMJW | PAPMJW |
| PAMYFJ | PATINT | PAPNWH | PAPNWH |
| PASYIE | PAPMJW | | |
| PANRSR | PANIUJ | | |
| PARDEL | PAPNWH | | |
| PAPAJT | PANJJE | | |
| PAREBH | PANRVB | | |
| PANWUW | | | |
| PAPEXA | | | |
| PAPAKV | | | |
| PARCAH | | | |
| PAPEYT | | | |
| PAPRVT | | | |
| PATINT | | | |
| PAPRNV | | | |
| PAPRYB | | | |
| PAPPYS | | | |
| PAPMJW | | | |
| PANIUJ | | | |
| PAPNWH | | | |
| PANJJE | | | |
| PANRVB | | | |

FIG. 1

| COG Study AALL0331: Standard Risk B-ALL | | | | | | | Induction Day 0 (%) | | Induction Day 28 (%) | | | |
|---|---|---|---|---|---|---|---|---|---|---|---|---|
| Pt | Patient USI | Age/Sex | WBC | CNS | B-ALL | Karyotype/FISH PROBE RESULTS | 179a-PE | 179a-FITC | 179a-PE | 179a-FITC | MRD | EFS |
| 1 | PAPUNM | 1/M | 31 | 1 | Pro | 46,XY,t(4;11)(q21;q23)[16]/46,XY[4] KMT2A-R | 54.7 | -- | -- | -- | -- | Alive |
| 2 | PARJSL | 3/F | 3.58 | 1 | Pre | 48,XX,r(10)(p15q26),+21,+21c[11]/47,XX,+21c[9] | 43.2 | 26.4 | 11.2 | 2.7 | 1.2 | Alive |
| 3 | PANTRP | 5/F | | | Pre | ETV6/RUNX1 | 53.9 | -- | -- | -- | -- | Alive |
| 4 | PAPKGP | 2/F | 10.2 | 2a | Pre | 53,XX,+4,+6,+14,+17,+18,+19,+21[13]/46,XX[3] | 65.5 | -- | -- | -- | -- | Alive |
| 5 | PANZGJ | 2/M | 16.21 | 1 | Pre | 53,XY,+X,+4,+6,+10,+14,+21,+21[cp3]/52,idem,del(4)(q13.2),-6,del(10)(q24)[15]/46,XY[2] | 12.5 | 26.0 | 2.6 | 2.0 | 1.1 | Alive |
| 6 | PAPHLN | 8/F | 37.3 | 1 | Pre | uninformative | 75.4 | 31.3 | 10.4 | 20.6 | 6.3 | Alive |
| 7 | PAPUDR | 3/M | 7.3 | 1 | Pre | 46,XY[20] | 39.8 | 23.6 | 63.5 | 34.0 | 44.5 | Alive |
| 8 | PASZFV | 3/M | 22.9 | 1 | Pre/20s | 51,XY,+X,+4,+14,+21,+21[19]/46,XY[6] | 46.2 | 39.2 | 1.4 | 56.1 | 7.5 | Lost |
| 9 | PARBXX | 5/M | 47 | 3c | Pre/20+ | 46,XY[21] | 45.0 | 14.0 | 4.0 | 14.9 | 2.4 | Dead |
| 10 | PAPVEG | 2/M | 39.6 | 3a | Pre/20+ | 46,XY[20] | 68.5 | -- | -- | -- | -- | Dead |
| 11 | PATEJI | 7/M | 1.9 | 1 | Pre/20+ | 46,XY[20] | 58.8 | 37.1 | 0.4 | 31.5 | 1.1 | Lost |

| COG Study AALL0232: High Risk B-ALL | | | | | | | Induction Day 0 (%) | | Induction Day 28 (%) | | | |
|---|---|---|---|---|---|---|---|---|---|---|---|---|
| Pt | Patient USI | Age/Sex | WBC | CNS | Stage | Karyotype | 179a-PE | 179a-FITC | 179a-PE | 179a-FITC | MRD | EFS |
| 12 | PANEBL | 1/F | 79.8 | 1 | Pro | 46,XX,der(11)inv(11)(p13p15)inv(11)(q12q23)del(11)(q14q23)[7]/46,XX[2] KMT2A-R | 33.4 | 32.4 | -- | -- | -- | Alive |
| 13 | PAPDNB | 16/M | 487.4 | 1 | Pro | 46,XY,t(9;22)(q34;q11.2)[20] BCR/ABL1 | 17.2 | 37.6 | 8.3 | 68.1 | 66 | Dead |
| 14 | PANPZS | 16/M | 5.5 | 1 | Pro | uninformative | 51.6 | 15.5 | -- | -- | -- | Lost |
| 15 | PARTCY | 6/F | 58.5 | 1 | Pre | 47,XX,der(2;9)(q10;q10),-7,+10,del(17)(q23),add(22)(q13),+mar1,+mar2[13]/46,XX[7] | 41.3 | -- | -- | -- | -- | Dead |
| 16 | PAMYFJ | 5/M | 133 | 1 | Pre | 46,XY,del(3)(p13p21),der(9;12)(p13;q11.2)[4]/46,XX[16] | 60.2 | 39.6 | 4.1 | 50.2 | 4.36 | Lost |
| 17 | PASYIE | 14/M | 3.7 | 1 | Pre | 57,XY,+X,+4,+5,+6,i(7)(q10),+9,+10,+14,+16,der(16)t(1;16)(q21;q12.2),+17,+18,+21[20] | 74.1 | -- | -- | -- | -- | Alive |
| 18 | PANRSR | 16/M | 10.2 | 1 | Pre | uninformative | 90.0 | 22.0 | 39.0 | 29.0 | 1.5 | Lost |
| 19 | PARDEL | 16/M | 80.5 | 1 | Pre | 46,XY[40] | 73.9 | -- | -- | -- | -- | Dead |
| 20 | PAPAJT | 8/M | 115.1 | 1 | Pre | 46,XY,del(6)(q13q21)[4]/46,XY[22] | 67.5 | 40.5 | 69.9 | 38.0 | 4.6 | Alive |
| 21 | PAREBH | 18/M | 171.2 | 2b | Pre | 47,XY,+21c[20] | 64.3 | -- | -- | -- | -- | Dead |
| 22 | PANWUW | 11/M | 23.9 | 1 | Pre | 46,XY,t(17;19)(q22;p13.3)[18]/46,XY[2] | 87.6 | -- | -- | -- | -- | Dead |
| 23 | PAPEXA | 2/M | 54.5 | 1 | Pre | TEL/AML1 | 32.9 | 43.0 | 13.0 | 50.2 | 1.2 | Alive |
| 24 | PAPAKV | 7/M | 388.3 | 1 | Pre | BCR/ABL1 | 68.9 | -- | -- | -- | -- | Alive |

FIG. 2A

| COG Study AALL0232: High Risk B-ALL | | | | | | | Induction Day 0 (%) | | | Induction Day 28 (%) | | | | |
|---|---|---|---|---|---|---|---|---|---|---|---|---|---|---|
| Pt | Patient USI | Age/Sex | WBC | CNS | Stage | Karyotype | 179a-PE | 179a-FITC | 179a-PE | 179a-FITC | MRD | EFS |
| 25 | PARCAH | 8/M | 117 | 1 | Pre | 46,XX,t(9;22)(q34.q11.2)[21] BCR/ABL1 | 0.0 | 24.2 | 0.7 | 38.5 | 43 | Alive |
| 26 | PAPEYT | 13/M | 101.1 | 2a | Pre | 46,XY,add(9)(p22)[cp5]/46,XY[18] | 69.9 | --- | --- | --- | | Lost |
| 27 | PAPRVT | 13/F | 24 | 1 | Pre | uninformative | 63.0 | --- | --- | --- | | Lost |
| 28 | PATINT | 5/M | 231 | 1 | Pre | 46,XY[20] | 95.2 | 46.7 | 3.8 | 20.1 | 9.2 | Dead |
| 29 | PAPRNV | 10/M | 214.2 | 1 | Pre | 47,Y,t(X;11)(p22.3;q13),del(6)(q23q25),i(9)(q10), t(9;22)(q34;q11.2),+der(22)t(9;22)[8]/46,XY[12] BCR/ABL1 | 36.9 | --- | --- | --- | | Alive |
| 30 | PAPRYB | 6/M | 63.1 | 2a | Pre | 48,XY,+X,i(17)(q10),+21[10]/46,XY[13] | 63.4 | --- | --- | --- | | Dead |
| 31 | PAPPYS | 7/M | 375.2 | 2a | Pre | 46,XY,t(9;22)(q34;q11.2)[15]/46,idem,del(1) (p34),t(5;13)(q35;q12)[5] BCR/ABL1 | 56.4 | --- | --- | --- | | Alive |
| 32 | PAPMJW | 14/M | 5 | 1 | Pre/20s | uninformative | 55.0 | 15.9 | 52.2 | 12.2 | 1.4 | Lost |
| 33 | PANIUJ | 15/M | 114.3 | 1 | Pre/20s | 46,XY,der(9)inv(9)(p13q32)del(9)(p13p24), inv(22)(q11.1q11.2)[13]/46,XY[7] | 90.6 | 19.8 | --- | --- | | Dead |
| 34 | PAPNWH | 24/M | 4.5 | 1 | Pre/20+ | 46,XY[21] | 0.2 | 33.0 | 9.1 | 66.7 | 5.5 | Lost |
| 35 | PANJJE | 15/M | 272 | 1 | Pre/20+ | uninformative | 52.4 | 20.2 | --- | --- | | Dead |
| 36 | PANRVB | 12/F | 71.1 | 2b | Pre/20+ | uninformative | 82.8 | 32.7 | --- | --- | | Dead |

FIG. 2A (Cont.)

| Supplemental Table 3 | | PAPDNB (Ph +) | PAPEYT (Ph-Like) | PAPNWH (PAX5alt) | Controls: 630 Ph+, Ph-like, PAX5alt cases | |
|---|---|---|---|---|---|---|
| Pre-BCR Components | | Pro-B | Pre-B | Pre-B CD20+ | Median | Range |
| IgH Component | Symbol | | | | | |
| ENSG00000253709.1 | IGHV1-14 | 2.3904 | 9.5443 | -3.3219 | -3.322 | (-3.322~11.959) |
| ENSG00000274576.2 | IGHV2-70 | 3.6195 | 10.1889 | 1.9930 | 3.478 | (-3.322~12.706) |
| ENSG00000270550.1 | IGHV3-30 | 8.1130 | 5.8894 | 5.7781 | 7.145 | (-3.322~14.721) |
| ENSG00000253989.2 | IGHVIII-38-1 | 6.8074 | 3.4671 | -3.3219 | -3.3219 | (-3.32~10.78) |
| ENSG00000229092.2 | IGHV3-47 | -3.3219 | -3.3219 | 10.0536 | -3.322 | (-3.32~10.05) |
| ENSG00000225698.3 | IGHV3-72 | 2.5396 | 4.6846 | 11.6097 | 3.774 | (-3.322~11.61) |
| ENSG00000211898.7 | IGHD | 4.9873 | 9.1696 | 9.3515 | 7.832 | (-2.291~12.486) |
| SLC Component | Symbol | | | | | |
| ENSG00000254709.7 | IGLL56 | 1.4176 | 4.7522 | 3.4783 | 5.632 | -3.322~16.482 |
| ENSG00000169575.4 | VPREB1 | 9.9774 | 9.0486 | 10.2350 | 10.615 | -3.322~15.455 |

RNA-seq Log2FPKM values for major components genes in three patients samples. Bold indicates genes that are either IgH re-arranged or relevant to the preBCR complex. The median value and range of Log2FPKM for these genes were calculated for 630 samples of Ph+, Ph-like and PAX5alt subtypes used in reference #13 (Gu Z, Churchman ML, Roberts KG, et al. PAX5-driven subtypes of B-progenitor acute lymphoblastic leukemia. Nat Genet. 2019;51(2):296-307). FPKM: Fragments Per Kilo exon base per Million reads.

FIG. 2B

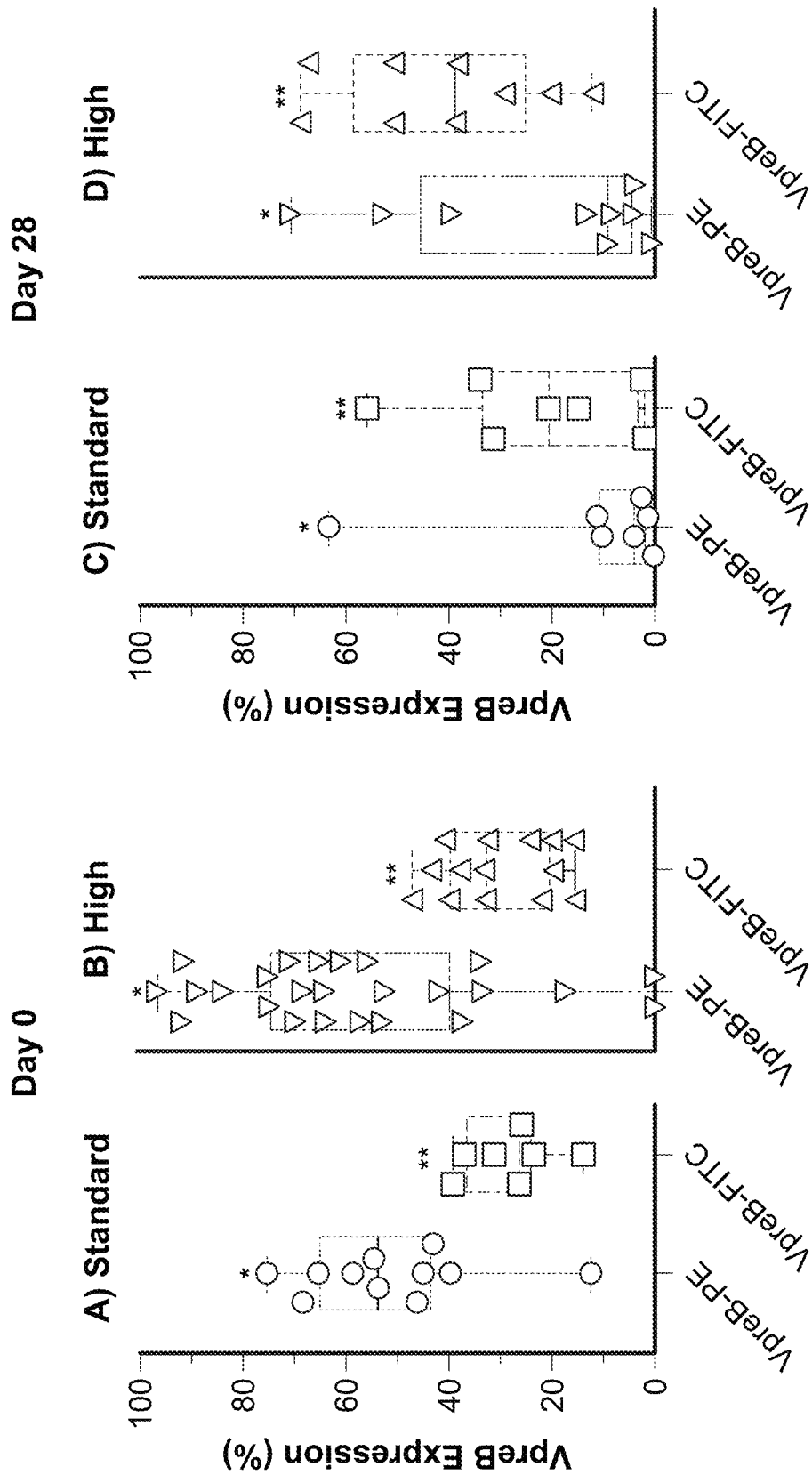

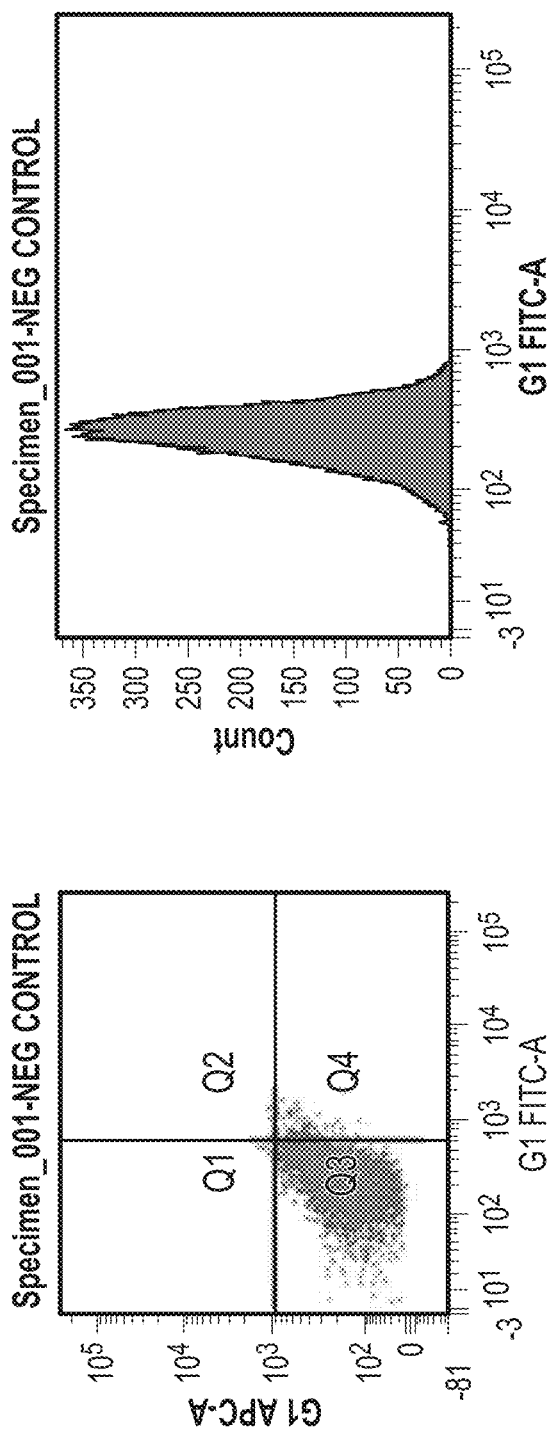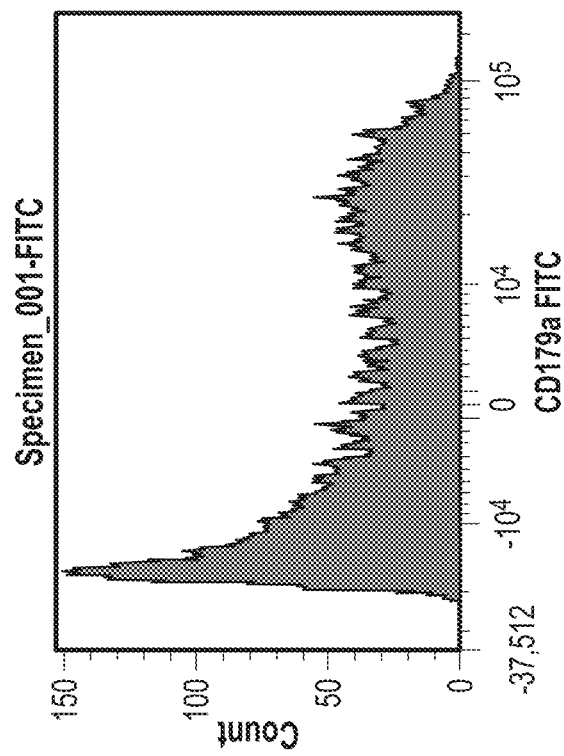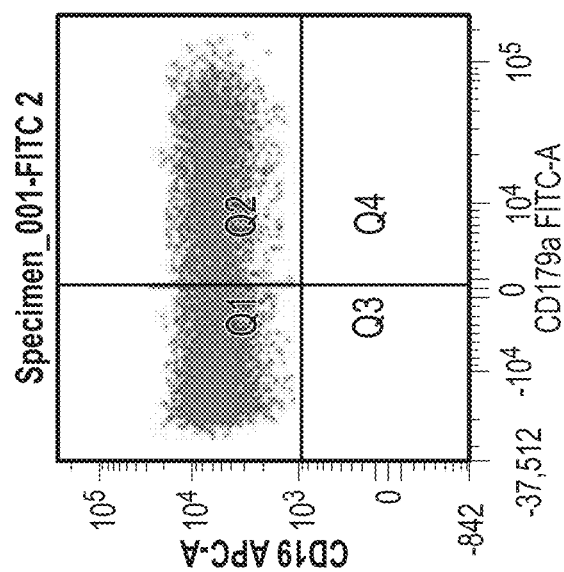
FIG. 5B

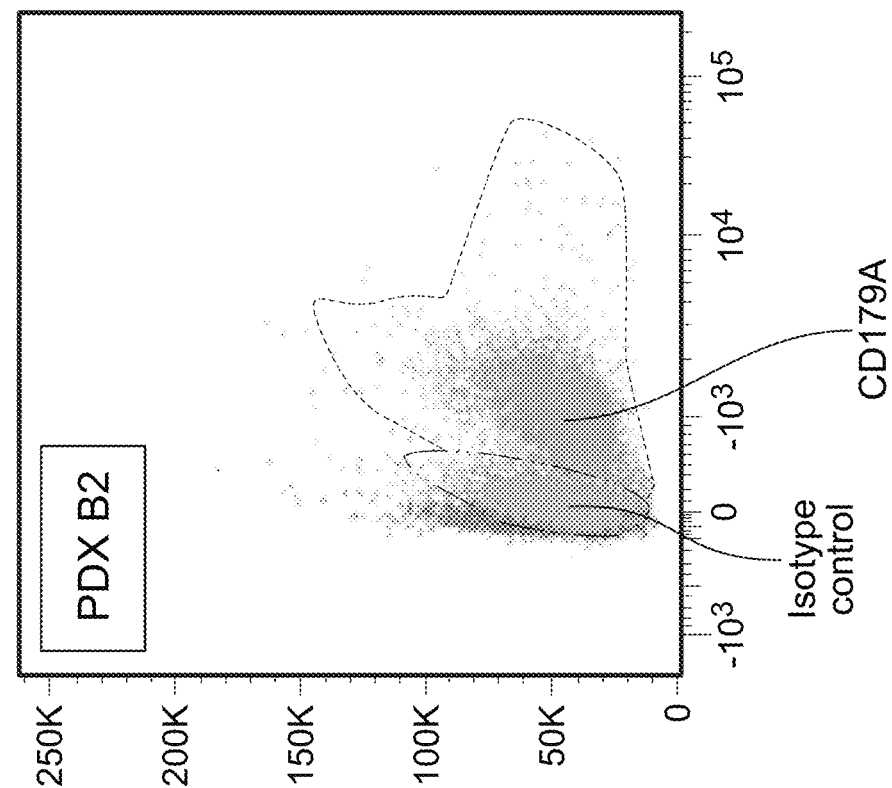
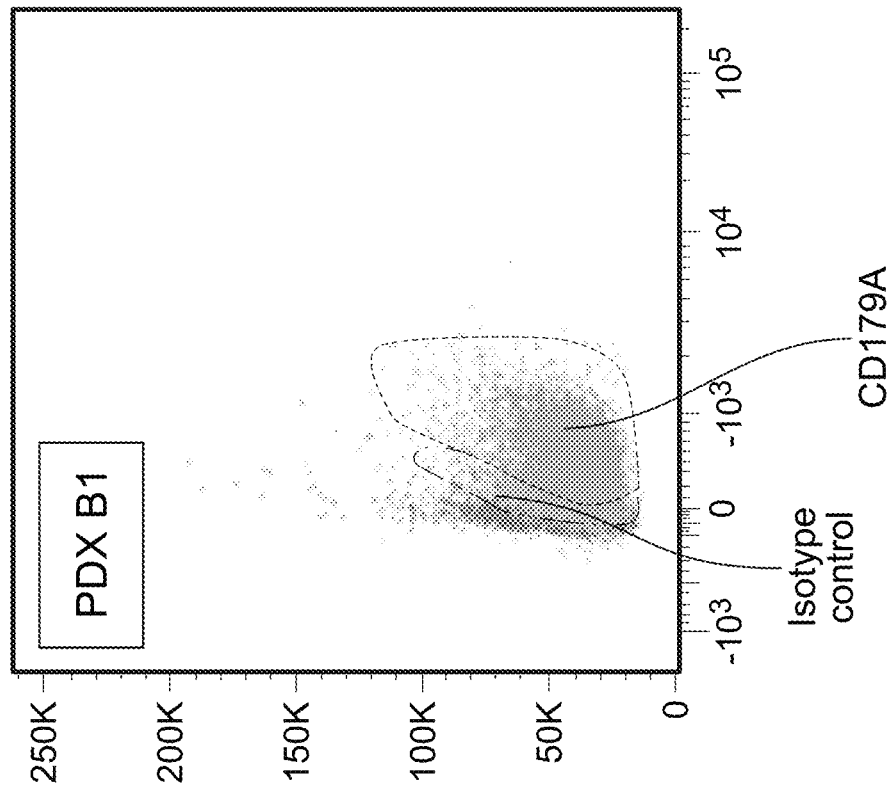
FIG. 7B

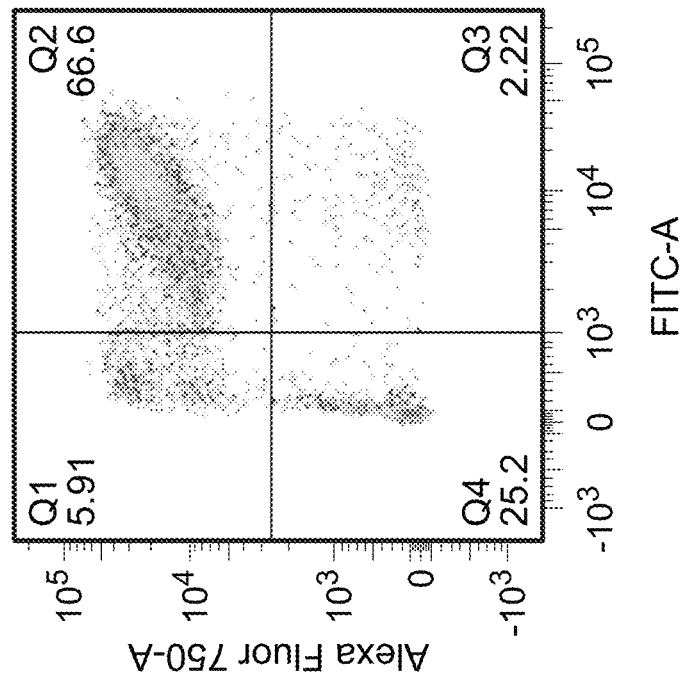
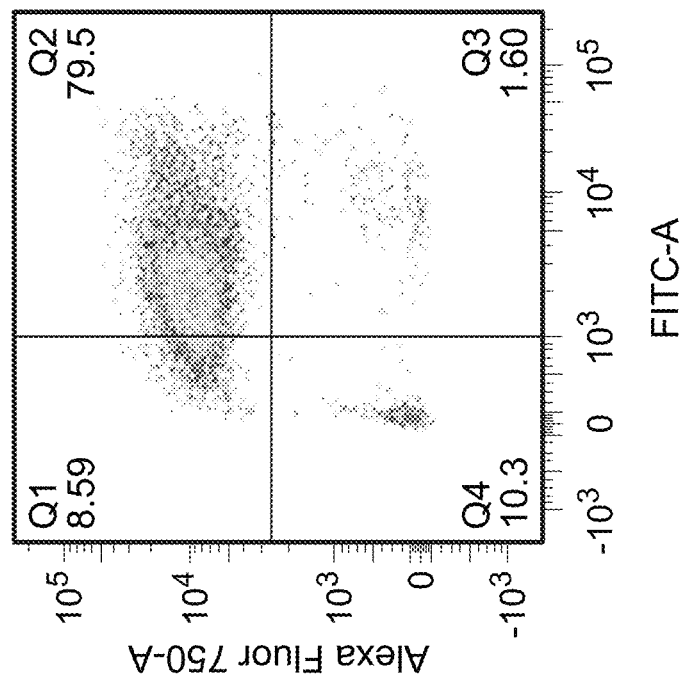
FIG. 9B

SEQUENCE LISTING

```
<160> NUMBER OF SEQ ID NOS: 18

<210> SEQ ID NO 1
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Trp Ser Cys Ile Ile Leu Phe Leu Val Ala Thr Ala Thr Gly
1               5                   10                  15
```

```
Val His Ser Glu Val Gln Leu Val Glu Ser Gly Gly Gly Leu Val Lys
            20                  25                  30
Pro Gly Gly Ser Leu Arg Leu Ser Cys Ala Ala Ser Gly Phe Thr Phe
            35                  40                  45
Ser Asn Phe Glu Met Asn Trp Val Arg Gln Ala Pro Gly Lys Gly Leu
            50                  55                  60
Glu Trp Val Ser Gly Ile Ser Ser Asn Gly Arg Tyr Ile Asn Tyr Ala
65                  70                  75                  80
Asp Ser Val Lys Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
                100                 105                 110
Tyr Tyr Cys Ala Arg Val Val Asp Phe Asp Gln Asp Tyr Asn Gly Phe
            115                 120                 125
Asp Tyr Trp Gly Gln Gly Thr Leu Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
            210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
            290                 295                 300
Gly Val Glu Val His Asn Ala Lys Thr Lys Pro Arg Glu Glu Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Asp Glu Leu Thr Lys Asn
            370                 375                 380
Gln Val Ser Leu Thr Cys Leu Val Lys Gly Phe Tyr Pro Ser Asp Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
                420                 425                 430
Thr Val Asp Lys Ser Arg Trp Gln Gln Gly Asn Val Phe Ser Cys Ser
```

435                 440                 445
Val Met His Glu Ala Leu His Asn His Tyr Thr Gln Lys Ser Leu Ser
        450                 455                 460

Leu Ser Pro Gly Lys
465

<210> SEQ ID NO 2
<211> LENGTH: 1439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaattcccgc cgccaccatg ggctggtcct gtatcatcct gttcctggtc gccacagcca      60
ccggagtgca cagcgaggtg cagctggtgg aaagcggagg cggcctggtt aagcccggcg     120
gatctctgag actgtcttgt gctgccagcg gcttcacctt cagcaacttc gagatgaact     180
gggtgcggca ggcccctggc aagggactgg aatgggtcag cggcatcagc tctaatggca     240
gatacatcaa ctacgccgac agcgtgaaag gccgcttcac aatctccaga gataacgcca     300
agaacagcct ctacctgcaa atgaatagcc tgcgggccga ggacaccgcc gtgtactact     360
gcgccagagt ggtggacttg accaggacta acggctttt gattattggg gccagggcac      420
actggtgacc gtgtccagcg ccagcaccaa gggcccctct gtctttcctc tggcccttc     480 tagcaaatct acaagcggag caccgccgc cctgggttgt ctggtgaaag actacttccc     540
agagcctgtg accgtgtctt ggaacagcgg cgccctgacc agcggcgtgc acacattccc     600
cgctgtgctg cagagcagcg gcctgtacag cctgagcagc gtggtcaccg tcccagcag     660 ctctctggga acacagacct acatctgcaa cgtgaaccac aagccttcta ataccaaggt     720
ggataagaag gtggaaccta agagttgcga caagacccac acctgtcctc cgtgccccgc     780
ccctgagctg ctgggcggcc ctagcgtgtt tctgttccct ccaaagccca aggacaccct     840
gatgatcagc agaaccctg aggtgacctg cgtggtggtt gatgtgtccc acgaagatcc      900
tgaggtgaag ttcaactggt acgtggacgg cgttgaggtg cataatgcca agacaaagcc     960
aagagaggaa cagtacaaca gcacatacag agtggtgtcc gtgctgaccg tgctgcacca    1020
ggactggctg aacggcaaag agtacaagtg caaggtgtcc aacaaggccc tgcctgctcc    1080
tatcgagaag accatcagca aggctaaagg acagcctcgg gaaccccagg tctacaccct    1140
gccccccagc cgggacgagc tgacaaagaa ccaggtgtcc ctgacatgcc tggtgaaggg    1200
cttctacccc tccgacatcg ccgtggaatg ggagagcaat ggccaacctg aaaacaacta    1260
caaaacgacc cctcctgttc tggacagcga cggcagcttc ttcctttata gcaagctgac    1320
agtggacaag agcagatggc agcagggcaa cgtgttcagc tgcagcgtga tgcacgaggc    1380
cctccacaac cactacaccc agaagtccct gagcctgtct cctggcaagt gataagctt     1439

<210> SEQ ID NO 3
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Trp Ser Cys Ile Ile Leu Phe Leu Val Ala Thr Ala Thr Gly

```
1               5                   10                  15
Val His Ser Asp Ile Gln Leu Thr Gln Ser Pro Ser Phe Leu Ser Ala
                20                  25                  30
Ser Val Gly Asp Arg Val Thr Ile Thr Cys Arg Ala Ser Gln Gly Ile
                35                  40                  45
Ser Thr Asp Leu Asn Trp Tyr Gln Gln Lys Pro Gly Lys Ala Pro Lys
            50                  55                  60
Leu Leu Ile Tyr Ala Ala Ser Asn Leu Glu Ser Gly Val Pro Ser Arg
65                  70                  75                  80
Phe Ser Gly Ser Gly Ser Gly Thr Glu Phe Thr Leu Thr Ile Ser Ser
                85                  90                  95
Leu Gln Pro Glu Asp Phe Ala Thr Tyr Tyr Cys Gln Gln Ser Tyr Asn
                100                 105                 110
Trp Pro Tyr Thr Phe Gly Gly Gly Thr Lys Val Glu Ile Lys Arg Thr
                115                 120                 125
Val Ala Ala Pro Ser Val Phe Ile Phe Pro Pro Ser Asp Glu Gln Leu
            130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
                180                 185                 190
Ser Leu Ser Ser Thr Leu Thr Leu Ser Lys Ala Asp Tyr Glu Lys His
                195                 200                 205
Lys Val Tyr Ala Cys Glu Val Thr His Gln Gly Leu Ser Ser Pro Val
            210                 215                 220
Thr Lys Ser Phe Asn Arg Gly Glu Cys
225                 230

<210> SEQ ID NO 4
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gaattcccgc cgccaccatg ggctggtcct gcatcatcct gttcctggtg gccacagcca      60
ccggcgtgca cagcgatatc cagctgaccc agagccccag ctttctgagc gccagcgtgg     120
gcgaccgggt caccatcacc tgtagagcct ctcagggcat ctccaccgac tcaactggta     180
tcagcagaa acctggcaag gcccctaagc tgctgatcta cgccgcttct aatctggaaa      240
gcggcgtgcc atctagattc agcggctccg gcagcggcac cgagttcacc ctgacaatta     300
gcagcctgca gcctgaggac ttcgccacat actactgcca gcaaagctac aactggccct     360
acaccttcgg cggaggaaca aaggtggaaa tcaagagaac cgtggccgcc cctagcgtgt     420
tcatcttccc cccagcgac gagcagctga gagcggtac agcttctgtg gtgtgcctgc      480
tgaacaactt ctacccgcgg gaagccaagg tgcagtggaa ggtggacaac gccctgcaga     540
gcggcaacag ccaggagagc gtgacagagc aggacagcaa ggacagcacc tacagcctga     600
gcagcaccct gaccctgagc aaggccgact acgagaagca caaggtgtac gcctgtgaag     660
tgacccacca gggcctgtct agccctgtga ccaagtcttt taacagaggc gagtgctgat     720
```

```
<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Phe
            20                  25                  30

Glu Met Asn Trp Val Arg Gln Ala Pro Gly Lys Gly Leu Glu Trp Val
        35                  40                  45

Ser Gly Ile Ser Ser Asn Gly Arg Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Val Asp Phe Asp Gln Asp Tyr Asn Gly Phe Asp Tyr Trp
            100                 105                 110

Gly Gln Gly Thr Leu Val Thr Val
        115                 120

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Asp
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Asn Trp Pro Tyr
                85                  90                  95

Thr Phe Gly Gly Gly Thr Lys Val Glu Ile Lys
            100                 105

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Asn Phe Glu Met Asn
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Ser Ser Asn Gly Arg Tyr Ile Asn Tyr Ala Asp Ser Val Lys
1               5                   10                  15

Gly

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Val Val Asp Phe Asp Gln Asp Tyr Asn Gly Phe Asp Tyr
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Gly Ile Ser Thr Asp Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Ser Tyr Asn Trp Pro Tyr Thr
1               5

<210> SEQ ID NO 13
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asn Phe Glu
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ser Ser Asn Gly Arg Tyr Ile
1               5

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Val Val Asp Phe Asp Gln Asp Tyr Asn Gly Phe Asp Tyr
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gly Ile Ser Thr Asp
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Gln Gln Ser Tyr Asn Trp Pro Tyr Thr
1               5
```

METHODS FOR TREATING B-ALL BY ADMINISTERING A PRE-BCR COMPLEX ANTAGONIST

CROSS-REFERENCE TO RELATED APPLICATIONS

This application is being filed on Feb. 15, 2022, as a U.S. Nonprovisional Patent Application and claims priority to U.S. Provisional Patent Application Nos. 63/149,728, entitled, "PRE-B CELL RECEPTOR EXPRESSION IN B-LINEAGE ACUTE LYMPHOBLASTIC LEUKEMIA", filed Feb. 16, 2021, and 63/278,030, entitled, "METHODS FOR TREATING B-ALL BY ADMINISTERING A PRE-BCR COMPLEX ANTAGONIST", filed Nov. 10, 2021; the contents of which are incorporated by reference in their entireties.

SEQUENCE STATEMENT

The instant application contains a Sequence Listing, which has been submitted electronically in ASCII format and is hereby incorporated by reference in its entirety. Said ASCII copy, created on Feb. 15, 2022, is named 00562-0049USU1-SEQLISTING.TXT and is 15 kilobytes in size.

FIELD OF THE DISCLOSURE

The present disclosure relates to the use of pre-B cell receptor (BCR) complex antagonists for treating B-cell acute lymphoblastic leukemia (B-ALL).

BACKGROUND

During B-cell development, the productively-assembled pre-B cell receptor (pre-BCR) autonomously signals to govern immature B-cell selection, survival, and maturation into immunoglobulin-producing cells (Reth and Nielsen, 2014 *Adv Immunol* 122:129-75). The pre-BCR is composed of five units: a membrane-bound V-, D-, J-recombined immunoglobulin heavy chain (IgH), an invariable, constant surrogate light chain (SLC) that is comprised of VpreB (CD179a) and λ5 (CD179) (Reth and Nielsen) and transmembrane Igα and Igβ (CD79a, b) accessory chains that co-assemble to provide intracellular signaling (Erasmus, et al., 2016 *Science Signaling* 9). Differentiation beyond the pro-B and pre-B cell stages can only occur when B-cell precursors have successfully undergone recombination with kappa or lambda light chains, which replace the SLC in maturing B-cells to create a functional BCR (Ubelhart, et al., 2010 *Nat Immunol* 11:759-65). These key differences between the pre-BCR and the mature BCR are illustrated in FIG. 13. Without pre-BCR mediated "tonic" autonomous signaling, immature B-cells undergo programmed cell death, but this critical selection step may be subverted by oncogenic transformation. (Reth and Nielsen, 2014 *Adv Immunol* 122:129-175; Buchner, et al., 2015 *Immunol Rev* 263(1):192-209).

B-lineage (or, B-cell) acute lymphoblastic leukemia (B-ALL) is the single most common cancer in infants, children, and young adults. Yet these vulnerable populations are often excluded from the clinical testing of novel agents. Despite a high degree of variability in genomic aberrations, nearly all B-ALL cases share a relatively restricted repertoire of B-cell surface markers that include CD79, CD45, CD19, CD22, and terminal deoxynucletidase, with variable expression of CD34 and CD20 (Hunger and Mullighan, 2015 *NEJM* 373:1541-52; Maury, et al., 2016 *NEJM* 373:1541-1552). The expression of CD10—or lack thereof—distinguishes pre-B-ALL from pro-B ALL, respectively (Chen, et al., 2016 *PLoS One* 11:e0162638). While a number of molecular, clinical, and treatment-response features are globally used to assign risk-adjusted therapies, relapse is a common problem among infants, adolescents, and across all stages of adulthood (Hunger and Mullighan; Gokbuget, 2018 *Drugs Aging* 35:11-26).

With the inclusion of post-induction minimal (also "measurable") residual disease (MRD) levels into risk-assignment algorithms, subsets of patients with high end-induction disease burden can be identified for whom novel or experimental therapies might reduce the risk for relapse (Hunger and Mullighan). Novel immunotherapies have the potential to uncover unexpected escape pathways by which leukemic cells evade cell death (Milanovic, et al., 2018 *Nature* 553:96-100). There is an important and unmet need for a specific, effective, and safer immunotherapy against B-ALL to prevent relapse, to minimize off-target toxicities, and to be more widely available to all affected patients.

Despite the critical importance of the pre-BCR in B-cell development, relatively little was previously known about the expression of this receptor complex in B-ALL. In preliminary analyses of pre-BCR biology and expression, others have concluded that the pre-BCR is functionally active in only a small subset of cases, calling for the designation "pre-BCR+ ALL" (Kohrer, et al., 2016 *Leukemia* 30:1246-54; Muschen. 2015 *Blood* 125:3688-3693). For antibody-mediated therapy, the target population is much broader, since a key criterion for targeting is surface expression, not signaling.

SUMMARY

A novel high-affinity, high avidity anti-pre-BCR antibody has been characterized, and it was evaluated whether blockade of homotypic pre-BCR self-associations might differentially sensitize primary patient samples to chemotherapy (Erasmus, et al., 2016 *Science Signaling* 9). The incubation of patient blasts with anti-VpreB mAbs was found to enhance apoptosis by de-coupling the autonomous cell signaling pathways that lead to B-cell survival (U.S. Pat. No. 10,988,533, incorporated herein in its entirety). Because B-ALLs might resist cytotoxic therapies by means of autonomous "tonic" survival signaling, it was investigated whether CD179a is more commonly expressed on B-lymphoblasts than previously reported (Kohrer, et al., 2016 *Leukemia* 30:1246-54). Immunotherapies targeted to restricted stages of B-cell development may also overcome the immunocompromise caused by the pan B-cell ablation of mature, antibody-producing cells. Flow-cytometric analyses and annotated patient clinical data were used to evaluate CD179a expression in primary patient samples that were accrued to modern COG B-ALL clinical trials for children and young adults.

Minimal residual disease (MRD) is highly prognostic in pediatric B-precursor acute lymphoblastic leukemia (B-ALL).

In one aspect, the disclosure provides a method for treating B-cell acute lymphoblastic leukemia (B-ALL) in a subject, comprising administering to the subject a pharmaceutical composition comprising a pre-B cell receptor (BCR) complex antagonist. In another aspect, the disclosure provides a method for treating B lymphoblastic lymphoma in a subject, comprising administering to the subject a pharmaceutical composition comprising a pre-B cell receptor (BCR) complex antagonist.

In one embodiment of a method according to the disclosure, the pre-BCR complex antagonist is a CD179a antagonist. CD179a is a distinct component of the pre-BCR complex. In a further embodiment, the CD179a antagonist is an antibody or antigen-binding fragment that specifically binds CD179a. In another embodiment, the anti-CD179a antibody or antigen binding fragment thereof comprises the heavy chain complementarity determining regions (HCDRs) of a heavy chain variable region (HCVR) having the amino acid sequence of SEQ ID NO:5 and the light chain complementarity determining regions (LCDRs) of a light chain variable region (LCVR) having the amino acid sequence of SEQ ID NO:6. In yet another embodiment, the anti-CD179a antibody or antigen binding fragment thereof comprises a heavy chain variable region (HCVR) comprising the amino acid sequence (CDRs underlined, Kabat annotation):

```
                                                       (SEQ ID NO: 5)
EVQLVESGGGLVKPGGSLRLSCAASGFTFSNFEMNWVRQAPGKGLEWVSGISSNGRYINY      60

ADSVKGRFTISRDNAKNSLYLQMNSLRAEDTAVYYCARVVDFDQDYNGFDYWGQGTLVTV     120
``` and a light chain variable region (LCVR) comprising the amino acid sequence (CDRs underlined, Kabat annotation):

```
                                                       (SEQ ID NO: 6)
DIQLTQSPSFLSASVGDRVTITCRASQGISTDLNWYQQKPGKAPKLLIYAASNLESGVPS      60

RFSGSGSGTEFTLTISSLQPEDFATYYCQQSYNWPYTFGGGTKVEIK.                 107
```

In another embodiment, the anti-CD179a antibody or antigen-binding fragment thereof comprises three heavy chain complementarity determining regions, HCDR1, HCDR2, and HCDR3 having the amino acid sequences of SEQ ID NOs:7, 8, and 9, respectively, and three light chain complementarity determining regions, LCDR1, LCDR2, and LCDR3 having the amino acid sequences of SEQ ID NOs:10, 11, and 12, respectively.

TABLE A

| | | |
|---|---|---|
| HCDR1 | SEQ ID NO: 7 | NFEMN |
| HCDR2 | SEQ ID NO: 8 | GISSNGRYINYADSVKG |
| HCDR3 | SEQ ID NO: 9 | ARVVDFDQDYNGFDY |
| LCDR1 | SEQ ID NO: 10 | RASQGISTDLN |
| LCDR2 | SEQ ID NO: 11 | AASNLES |
| LCDR3 | SEQ ID NO: 12 | QQSYNWPYT |
| Kabat | | |

In still another embodiment, the anti-CD179a antibody or antigen-binding fragment thereof comprises a heavy chain variable region (HCVR) comprising the amino acid sequence (CDRs underlined, IMGT annotation):

```
                                                       (SEQ ID NO: 5)
EVQLVESGGGLVKPGGSLRLSCAASGFTFSNFEMNWVRQAPGKGLEWVSGISSNGRYINY      60

ADSVKGRFTISRDNAKNSLYLQMNSLRAEDTAVYYCARVVDFDQDYNGFDYWGQGTLVTV     120
``` and a light chain variable region (LCVR) comprising the amino acid sequence (CDRs underlined, IMGT annotation):

```
                                                       (SEQ ID NO: 6)
DIQLTQSPSFLSASVGDRVTITCRASQGISTDLNWYQQKPGKAPKLLIYAASNLESGVPS      60

RFSGSGSGTEFTLTISSLQPEDFATYYCQQSYNWPYTFGGGTKVEIK.                 107
```

In another embodiment, the anti-CD179a antibody or antigen-binding fragment thereof comprises three heavy chain complementarity determining regions, HCDR1, HCDR2, and HCDR3 having the amino acid sequences of SEQ ID NOs:13, 14, and 15, respectively, and three light chain complementarity determining regions, LCDR1, LCDR2, and LCDR3 having the amino acid sequences of SEQ ID NOs:16, 17, and 18, respectively.

TABLE B

| HCDR1 | SEQ ID NO: 13 | GFTFSNFE |
| --- | --- | --- |
| HCDR2 | SEQ ID NO: 14 | ISSNGRYI |
| HCDR3 | SEQ ID NO: 15 | ARVVDFDQDYNGFDY |
| LCDR1 | SEQ ID NO: 16 | QGISTD |
| LCDR2 | SEQ ID NO: 17 | AAS |
| LCDR3 | SEQ ID NO: 18 | QQSYNWPYT |
| IMGT | | |

In yet another embodiment, the anti-CD179a antibody or antigen-binding fragment thereof comprises a heavy chain comprising the amino acid sequence of SEQ ID NO:1 and a light chain comprising the amino acid sequence of SEQ ID NO:3.

In one embodiment of a method according to the disclosure, the antagonist specifically binds B lineage leukemia cells. In another embodiment of a method according to the disclosure, the antagonist does not bind normal mature B cells. In specific embodiments, "normal" B cells are non-leukemic BCR-expressing lymphocytes.

In one embodiment of a method according to the disclosure, the subject is human. In another embodiment of a method according to the disclosure, the subject is adult. In yet another embodiment of a method according to the disclosure, the subject is pediatric.

In another embodiment of a method according to the disclosure, the composition is administered intravenously or subcutaneously to the subject. In still another embodiment of a method according to the disclosure, the composition is administered intravenously to the subject. In still another embodiment of a method according to the disclosure, the composition is administered via intravenous infusion to the subject. In a further embodiment, the composition is administered to the subject intravenously over about 15 to about 30 minutes.

In one embodiment of a method according to the disclosure, the composition is administered to the subject at a dose of about 1 mg/kg to about 10 mg/kg. In another embodiment, the composition is administered to the subject at a dose of about 1 mg/kg to about 5 mg/kg. In still another embodiment, the composition is administered to the subject at a dose of about 3 mg/kg. In still another embodiment, the composition is administered to the subject at a dose of about 2 mg/kg.

In one aspect, the disclosure provides a method for treating B-cell acute lymphoblastic leukemia (B-ALL) in a subject, comprising administering to the subject a pharmaceutical composition comprising an antibody-drug conjugate (ADC), wherein the antibody specifically binds CD179a. In another aspect, the disclosure provides a method for treating B lymphoblastic lymphoma in a subject, comprising administering to the subject a pharmaceutical composition comprising an antibody-drug conjugate (ADC), wherein the antibody specifically binds CD179a. In some embodiments of a method according to the disclosure, the antibody of the ADC is a fragment (including functional antigen-binding) or derivative of the same, for example, a single-chain fragment variable.

In one embodiment of a method according to the disclosure, the anti-CD179a antibody comprises the heavy chain complementarity determining regions (HCDRs) of a heavy chain variable region (HCVR) having the amino acid sequence of SEQ ID NO:5 and the light chain complementarity determining regions (LCDRs) of a light chain variable region (LCVR) having the amino acid sequence of SEQ ID NO:6.

In another embodiment of a method according to the disclosure, the anti-CD179a antibody comprises three heavy chain complementarity determining regions, HCDR1, HCDR2, and HCDR3 having the amino acid sequences of SEQ ID NOs:7, 8, and 9, respectively, and three light chain complementarity determining regions, LCDR1, LCDR2, and LCDR3 having the amino acid sequences of SEQ ID NOs:10, 11, and 12, respectively.

In another embodiment of a method according to the disclosure, the anti-CD179a antibody comprises a heavy chain variable region (HCVR) having the amino acid sequence of SEQ ID NO:5 and a light chain variable region (LCVR) having the amino acid sequence of SEQ ID NO:6.

In yet another embodiment, the anti-CD179a antibody comprises a heavy chain comprising the amino acid sequence of SEQ ID NO:1 and a light chain comprising the amino acid sequence of SEQ ID NO:3.

In one embodiment of a method according to the disclosure, the ADC specifically binds B lineage leukemia cells. In another embodiment of a method according to the disclosure, the ADC does not bind normal mature B cells.

In one embodiment of a method according to the disclosure, the drug (of the ADC) is calicheamicin.

In one aspect, the disclosure provides a pharmaceutical composition comprising a pre-B cell receptor (BCR) complex antagonist and a pharmaceutically acceptable carrier. In one embodiment of a composition according to the disclosure, the pre-BCR complex antagonist is a CD179a antagonist. In another embodiment of a composition according to the disclosure, the CD179a antagonist is an antibody or antigen-binding fragment that specifically binds CD179a.

In one embodiment of a composition according to the disclosure, the anti-CD179a antibody or antigen binding fragment thereof comprises the heavy chain complementarity determining regions (HCDRs) of a heavy chain variable region (HCVR) having the amino acid sequence of SEQ ID NO:5 and the light chain complementarity determining regions (LCDRs) of a light chain variable region (LCVR) having the amino acid sequence of SEQ ID NO:6. In another embodiment, the anti-CD179a antibody or antigen-binding fragment thereof comprises three heavy chain complementarity determining regions, HCDR1, HCDR2, and HCDR3 having the amino acid sequences of SEQ ID NOs:7, 8, and 9, respectively, and three light chain complementarity determining regions, LCDR1, LCDR2, and LCDR3 having the amino acid sequences of SEQ ID NOs:10, 11, and 12, respectively. In still another embodiment, the anti-CD179a antibody or antigen-binding fragment thereof comprises a heavy chain variable region (HCVR) comprising the amino acid sequence of SEQ ID NO:5 and a light chain variable region (LCVR) comprising the amino acid sequence of SEQ ID NO:6. In a further embodiment, the anti-CD179a antibody or antigen-binding fragment thereof comprises a heavy chain comprising the amino acid sequence of SEQ ID NO:1 and a light chain comprising the amino acid sequence of SEQ ID NO:3.

In one embodiment of a composition according to the disclosure, the antagonist binds B lineage leukemia cells. In another embodiment of a composition according to the disclosure, the antagonist does not bind normal mature B cells.

In one embodiment of a composition according to the disclosure, the subject is human. In another embodiment of a composition according to the disclosure, the subject is adult. In yet another embodiment of a composition according to the disclosure, the subject is pediatric.

In one embodiment of a composition according to the disclosure, the composition is for (or is formulated for) intravenous or subcutaneous administration to the subject.

In one embodiment of a composition according to the disclosure, the composition comprises about 1 mg/kg to about 10 mg/kg of the pre-BCR complex antagonist. In another embodiment, the composition comprises about 1 mg/kg to about 5 mg/kg of the antagonist. In still another embodiment, the composition comprises about 3 mg/kg of the antagonist.

In one embodiment, a composition according to the disclosure is for use in the treatment of B-cell acute lymphoblastic leukemia (B-ALL). In another embodiment, the composition is for use in the treatment of B lymphoblastic lymphoma.

In one aspect, the disclosure provides an antibody-drug conjugate (ADC), wherein the antibody specifically binds CD179a.

In one aspect, the disclosure provides a pharmaceutical composition comprising an antibody-drug conjugate (ADC), wherein the antibody specifically binds CD179a, and a pharmaceutically acceptable carrier. In some embodiments of a composition according to the disclosure, the antibody of the ADC is a fragment (including functional antigen-binding) or derivative of the same, for example, a single-chain fragment variable.

In one embodiment of a conjugate or composition according to the disclosure, the anti-CD179a antibody comprises the heavy chain complementarity determining regions (HCDRs) of a heavy chain variable region (HCVR) having the amino acid sequence of SEQ ID NO:5 and the light chain complementarity determining regions (LCDRs) of a light chain variable region (LCVR) having the amino acid sequence of SEQ ID NO:6. In another embodiment, the anti-CD179a antibody comprises three heavy chain complementarity determining regions, HCDR1, HCDR2, and HCDR3 having the amino acid sequences of SEQ ID NOs:7, 8, and 9, respectively, and three light chain complementarity determining regions, LCDR1, LCDR2, and LCDR3 having the amino acid sequences of SEQ ID NOs:10, 11, and 12, respectively. In still another embodiment, the anti-CD179a antibody comprises a heavy chain variable region (HCVR) comprising the amino acid sequence of SEQ ID NO:5 and a light chain variable region (LCVR) comprising the amino acid sequence of SEQ ID NO:6. In a further embodiment, the anti-CD179a antibody comprises a heavy chain comprising the amino acid sequence of SEQ ID NO:1 and a light chain comprising the amino acid sequence of SEQ ID NO:3.

In one embodiment of a conjugate or composition according to the disclosure, the ADC binds B lineage leukemia cells. In another embodiment of a conjugate or composition according to the disclosure, the ADC does not bind normal mature B cells.

In one embodiment of a conjugate or composition according to the disclosure, the drug (of the ADC) is calicheamicin.

In one embodiment of a composition according to the disclosure, the composition is for (or is formulated for) intravenous administration to the subject. In still another embodiment of a composition according to the disclosure, the composition is administered via intravenous infusion to the subject. In a further embodiment, the composition is administered intravenously to the subject over about 15 to about 30 minutes.

In one embodiment of a composition according to the disclosure, the composition comprises about 1 mg/kg to about 10 mg/kg of the ADC. In another embodiment, the composition comprises about 1 mg/kg to about 5 mg/kg of the ADC. In still another embodiment, the composition comprises about 3 mg/kg of the ADC. A clinician can determine appropriate dosage for a subject based on parameters including, but not limited to, age, disease state, physical condition, disease burden, and/or tolerance for the ADC.

Other embodiments will be apparent from a review of the ensuing detailed description.

BRIEF DESCRIPTION OF THE FIGURES

FIG. 1. Specimen tracking for flow-based CD179a mAb testing in Day 0 and Day 28 samples. Samples accrued to AALL0331 are shown in italics, and those accrued to AALL0232 are shown in bold font.

FIGS. 2A and 2B show tables listing (FIG. 2A) study information for the standard risk B-ALL patients and high risk B-ALL patients (PE-CD179a, Biolegend; FITC-CD179a (data expressed as % of CD-19 positive B-cell population); "uninformative"=no cytogenetics results due to culture failure; "--"=not available/not done; Bold=Percent positive cells gated for B cells expressing CD19, CD45 versus CD179a/italics=total cell population expressing CD179a; MRD=minimal residual disease measured by the COG reference lab); and (FIG. 2B) RNA-seq data for three of the patients. These data show that the IGH chain and surrogate light chain were expressed in the samples that were studied.

(FIG. 3A) CD179a-PE; (FIG. 3B) CD179a-FITC.

FIGS. 4A-4D show box-and-whisker plots of monoclonal antibody expression levels. VpreB expression in standard- and high-risk B-ALL at diagnosis (Day 0) and end-induction (Day 28). VpreB-PE (control) and VpreB-FITC (mAb employed in the composition and method according to the disclosure) in standard (FIG. 4A) and high-risk (FIG. 4B) showed a spectrum of expression, but brighter expression for the PE conjugate (P<0.001, unpaired t-test) at the time of diagnosis. VpreB-PE and VpreB-FITC in standard (FIG. 4C) and high-risk (FIG. 4D) showed a spectrum of expression, but trended to show brighter expression for the FITC conjugate (P<0.001, unpaired t-test) at end-induction, suggesting that the FITC conjugate might detect recovering marrow populations that include B-lymphoblast populations with leukemic cells and hematogones. Statistical comparisons were calculated between combined PE* and FITC** groups.

FIGS. 5A and 5B show flow-based analyses of pre-BCR (CD179a component) expression. (FIG. 5A) representative histograms for three representative primary B-ALL Day1/Day28 dyadic pairs using PE- and FITC-conjugated CD179a mAbs. All cases show arrest at the pre-B cell developmental stage and robust CD179a expression as measured by the FITC-labeled mAb. Although the B-lymphoblast population was comparatively smaller in the end-induction cases than at diagnosis, all showed CD179a positivity in the residual B-lymphoblast population. From testing available from the COG Reference laboratories, the end-induction MRD levels for the PAPAJT (46,XY,del(6)(q13q21)[4]/46,XY[22]), PAPEXA (TEL/AML1) and PAPMJW (Culture Fail) was 4.6%, 1.2% and 1.4%, respectively. (FIG. 5B) Negative and positive control experiments using Nalm-6 cells. (top 2 plots) FITC-IgG1 negative control mAb; (bottom 2 plots) FITC-IgG1 CD179a mAb (Abcam conjugation kit). The FITC-CD179a mAb internalized, whereas the PE-conjugated CD179a mAb (Biolegend) did not.

FIGS. 7A and 7B show the expression of CD179a in various B-lineage cell lines (FIG. 7A: B-ALL cell lines Nalm6, REH, SEM and FIG. 7B: B-ALL PDX cell lines PDX B1, PDX B2.

FIGS. 9A and 9B show flow histograms for B-lineage cell lines Nalm6 and REH (FIG. 9A) after treatment with antibody alone vs. (FIG. 9B) after treatment with the ADC.

DETAILED DESCRIPTION

Figures 3A, 3B:
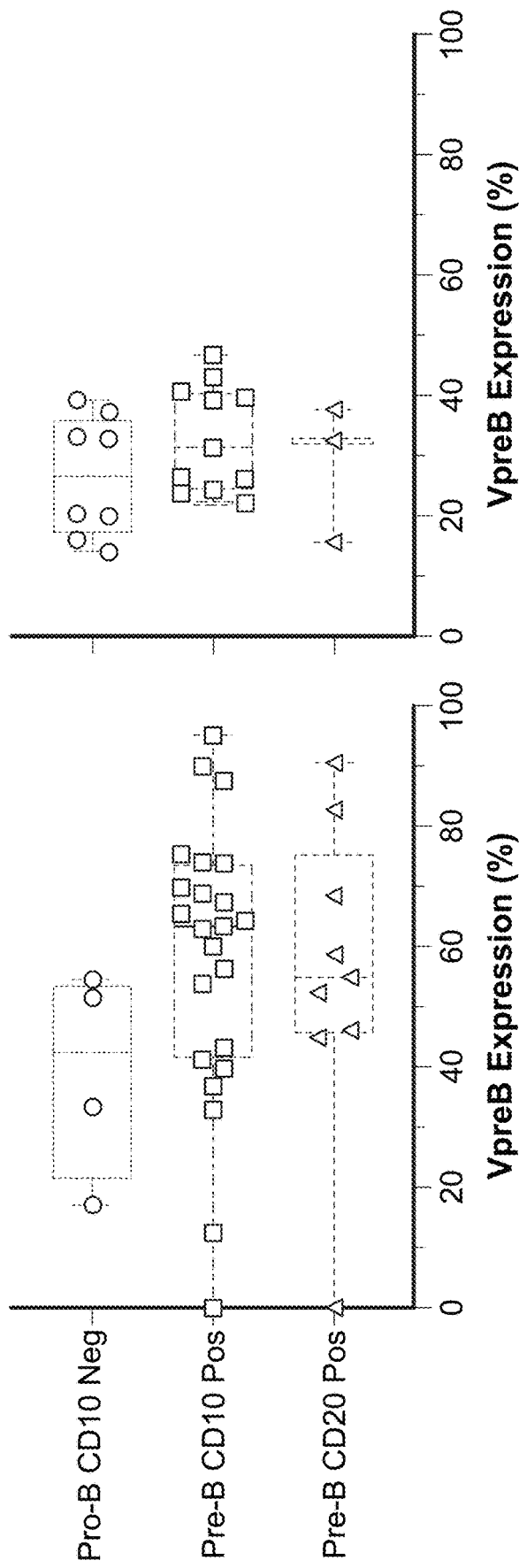
FIGS. 3A and 3B shows box-and-whisker plots of monoclonal antibody expression levels. Using the VpreB-PE (Biolegend mAb), 36 diagnostic cases were tested for VpreB surface expression in Day 0 cryopreserved samples that were obtained from children and young adults with NCI standard and high-risk B-ALL. Cases were subdivided into pro-B and pre-B ALL based upon the absence or presence of co-expression with CD10 and CD20. There were no statistical differences in VpreB expression among these three subgroups, but all cases except four showed >20% expression using the PE-conjugated CD179a mAb. Lack of VpreB expression could not be correlated with the presence or absence of any recurring molecular aberrations shown in FIG. 2A.

Before the present invention is described, it is to be understood that the invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

As used herein, the term "subject in need thereof" refers to a human or a non-human animal having B-cell acute lymphoblastic leukemia (B-ALL) or having B lymphoblastic lymphoma or being at risk for developing B-cell acute lymphoblastic leukemia (B-ALL) or being at risk for developing B lymphoblastic lymphoma. The terms "subject" and "patient" are used interchangeably herein.

Although any methods and materials similar or equivalent to those described herein can be used in the practice of the disclosure, the typical methods and materials are now described. All publications mentioned herein are incorporated herein by reference in their entirety.

Therapeutic Methods

In one aspect, the disclosure provides methods for treating B-cell acute lymphoblastic leukemia (B-ALL). In specific embodiments, treatment of B-ALL comprises reduction of B-cell acute lymphoblastic leukemia (B-ALL) relapse and/or progression. In further embodiments, the pharmaceutical compositions and methods disclosed herein are used for treating pediatric B-ALL. The disclosure also provides methods for treating B lymphoblastic lymphoma.

B-cell acute lymphoblastic leukemia (B-ALL) is also referred to as B-cell precursor acute lymphoblastic leukemia (BCP-ALL). When a neoplasm of lymphoblasts committed to the B-cell lineage, typically composed of small to medium-sized blast cells, involves predominantly the bone marrow and the peripheral blood, it is called B-cell acute lymphoblastic leukemia; when it involves nodal or extranodal sites, it is called B lymphoblastic lymphoma.

In another embodiment, treatment of B-ALL comprises improvement in a parameter associated with B-ALL. To determine whether a B-ALL-associated parameter has "improved," the parameter is quantified at baseline and at one or more time points after administration of the pharmaceutical composition described herein. The difference between the value of the parameter at a particular time point following initiation of treatment and the value of the parameter at baseline is used to establish whether there has been an "improvement" (e.g., a decrease) in the disease-associated parameter. In certain embodiments, the B-ALL-associated parameter employed as a measure of disease response to treatment is remission, for example, as measured by <5% blasts in the bone marrow compartment, absence of disease in the central nervous system compartment "(CNS1)", and/or no measureable disease in any other non-marrow compartment (for example, no other active sites of involvement, such as a pleural effusion, soft tissue mass, or adenopathy of >1.5 cm in the largest diameter, nor signs of hepato-splenomegally). In further embodiments, the B-ALL-associated parameter employed as a measure of disease response to treatment is progress toward remission, for example, as measured by a measurable reduction in blasts in the bone marrow compartment, measurably reduced disease in the central nervous system compartment "(CNS1)", and/or a reduction in measureable disease in any other non-marrow compartment (for example, less other active sites of involvement, such as a pleural effusion, soft tissue mass, or adenopathy of >1.5 cm in the largest diameter, or signs of hepato-splenomegally). In a further embodiment, minimal (also, "measurable") residual disease (MRD) can identify sub-sets of patients for whom novel or experimental therapies, including the therapies disclosed herein, might prevent relapse.

Relapse is a common problem for patients with high-risk disease. While useful as a stratification tool, the molecular and cellular mechanisms that mediate MRD are not well understood. To overcome the multi-drug resistance that stems from cytotoxic therapies, immunotherapies have been engineered against B-ALL surface proteins, some with successful results. B-ALLs relapsing after immunotherapies demonstrate surface antigen remodeling, down-regulation, permanent lineage switch to antigen non-expressing states, and T-cell exhaustion.

In certain embodiments, the pharmaceutical compositions and methods disclosed herein are used for treating B-ALL in subjects who are refractory to other treatment, or for whom other treatment has failed. In further embodiments, the pharmaceutical compositions and methods disclosed herein may provide treatment choices for B-ALL/lymphoma subjects as a front-line treatment at any point in the treatment course.

In further embodiments, the pharmaceutical compositions and methods according to the disclosure preserve the B-cell repertoire and/or reduce immunocompromise. Because CD179a is shown herein to be more commonly expressed on B-lymphoblasts than previously thought, immunotherapies targeted to restricted stages of B-cell development may overcome the limitations of pan B-cell ablation.

In further embodiments, the pharmaceutical compositions and methods according to the disclosure can directly mitigate the phenomenon of minimal residual disease.

Pre-BCR Antagonists

The novel B-cell marker, CD179a (VbreB1), is a component of the surrogate light chain, that controls autonomous cell survival and is expressed in all stages of B-ALL (Winter, et al., 2022 Blood Adv 6(2):585-589). Thus, this cell-based signaling program may be involved in governing the phenomenon of MRD in B-ALL.

CD179a is an 18 kD Ig V-like protein expressed on pro-B and early pre-B cells. It is a member of the Ig gene superfamily, known as VpreB, VPREB1, and IGVPB. CD179a noncovalently associates with CD179b ($\lambda$5) to form a surrogate light (SL) chain. The SL chain is complexed with membrane bound IgM heavy ($\mu$H) chain and CD79a/CD79b (Ig$\alpha$/I$\beta$) heterodimer to form the pre-B-cell receptor (Pre-BCR) complex.

In some embodiments, the methods of the present disclosure comprise administering to a subject in need thereof a pre-BCR complex antagonist. As used herein, a "pre-BCR complex antagonist" is any agent that binds to or interacts with the pre-BCR complex, and inhibits or attenuates, even if mildly, the normal biological function of the complex. In specific embodiments, a "pre-BCR complex antagonist" delivers a killing agent via binding to the pre-BCR complex, leads to leukemic cell death, and/or eliminates cells whose survival is dependent upon tonic signaling from the pre-BCR.

Non-limiting examples of categories of pre-BCR complex antagonists include agents that specifically bind CD179a, including antibodies or antigen-binding fragments of antibodies that specifically bind human CD179a.

Anti-CD179a Antibodies and Antigen-Binding Fragments Thereof

Because CD19, CD20, CD22 (and, less commonly, CD38) are ubiquitously expressed in B-cell neoplasms, these surface receptors are logical targets for cell-based therapies (Matlawska-Wasowska, et al., 2013 Leukemia; Maude and Barrett, 2016 Br J Haematol 172:11-22; Hunger and Mullighan, 2015 NEJM 373:1541-52; Bonifant and Tasian, 2020 Curr Opin Pediatr 32:13-25). However, trials utilizing an anti-CD20 mAb were limited in accrual and subsequent implementation into clinical practice by the rarity of CD20 expression in B-ALL (Maury, et al., 2016 NEJM 375:1044-1053). All B-lineage acute leukemia express the VpreB1 component in pre-B cell surrogate light chain receptor, regardless of genotype, which plays a critical role in the pro- and pre-B transitional stages in B-cell development (Winter, et al., 2021 Blood Adv). This surface ligand maintains autonomous signaling, which prevents B-cells from undergoing programmed cell death prior to light chain rearrangement for production of an assembled BCR. No current B-ALL immunotherapies specifically target the pro- and pre-B stages of B-cell development.

In certain exemplary embodiments of the present disclosure, the pre-BCR complex antagonist is an anti-CD179a antibody or antigen-binding fragment thereof. The IgG1 anti-VpreB1 mAb described herein is highly-specific to the pro- and pre-B stages of B-ALL.

Exemplary anti-CD179a antibodies are, for example, described in U.S. Pat. No. 10,858,448, incorporated herein in its entirety.

In one embodiment, the anti-CD179a antibody or antigen-binding fragment thereof comprises the heavy chain complementarity determining regions (HCDRs) of a heavy chain variable region (HCVR) having the amino acid sequence of SEQ ID NO:5 and the light chain complementarity determining regions (LCDRs) of a light chain variable region (LCVR) having the amino acid sequence of SEQ ID NO:6. In another embodiment, the anti-CD179a antibody or antigen-binding fragment thereof comprises the heavy chain complementarity determining regions (HCDRs) of a heavy chain variable region (HCVR) having an amino acid sequence having at least 95%, at least 96%, at least 97%, at least 98%, or at least 99% sequence identity with the amino acid sequence of SEQ ID NO:5 and the light chain complementarity determining regions (LCDRs) of a light chain variable region (LCVR) having an amino acid sequence having at least 95%, at least 96%, at least 97%, at least 98%, or at least 99% sequence identity with the amino acid sequence of SEQ ID NO:6.

In another embodiment, the anti-CD179a antibody or antigen-binding fragment thereof comprises three heavy chain complementarity determining regions, HCDR1, HCDR2, and HCDR3 having the amino acid sequences of SEQ ID NOs:7, 8, and 9, respectively, and three light chain complementarity determining regions, LCDR1, LCDR2, and LCDR3 having the amino acid sequences of SEQ ID NOs:10, 11, and 12, respectively. In still another embodiment, the anti-CD179a antibody or antigen-binding fragment thereof comprises three heavy chain complementarity determining regions, HCDR1, HCDR2, and HCDR3 having amino acid sequences having at least 95%, at least 96%, at least 97%, at least 98%, or at least 99% sequence identity with the amino acid sequences of SEQ ID NOs:7, 8, and 9, respectively, and three light chain complementarity determining regions, LCDR1, LCDR2, and LCDR3 having amino acid sequences having at least 95%, at least 96%, at least 97%, at least 98%, or at least 99% sequence identity with the amino acid sequences of SEQ ID NOs:10, 11, and 12, respectively.

In still another embodiment, the anti-CD179a antibody or antigen-binding fragment thereof comprises a heavy chain comprising the amino acid sequence of SEQ ID NO:1 and a light chain comprising the amino acid sequence of SEQ ID NO:3. In yet another embodiment, the anti-CD179a antibody or antigen-binding fragment thereof comprises a heavy chain comprising an amino acid sequence having at least 95%, at least 96%, at least 97%, at least 98%, or at least 99% sequence identity with the amino acid sequence of SEQ ID NO:1 and a light chain comprising an amino acid sequence having at least 95%, at least 96%, at least 97%, at least 98%, or at least 99% sequence identity with the amino acid sequence of SEQ ID NO:3.

```
SEQ ID NO: 1 CD179a IgG1/kappa construct
full-length heavy chain sequence (471 aa):
MGWSCIILFLVATATGVHSEVQLVESGGGLVKPGGSLRLSCAASGFTFSN

FEMNWVRQAPGKGLEWVSGISSNGRYINYADSVKGRFTISRDNAKNSLYL

QMNSLRAEDTAVYYCARVVDFDQDYNGFDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEYNSTYRVVSVLTVLHQDWLNGKEYKCKVSNKA

LPAPIEKTISKAKGQPREPQVYTLPPSRDELTKNQVSLTCLVKGFYPSDA

VEWESNGQPENNYKTTPPVLDSDGSFFLYSKLTVDKSRWQQGNVFSCSVM

HEALHNHYTQKSLSLSPGK

SEQ ID NO: 2 CD179a IgG1/kappa construct
heavy chain nucleotide sequence (1440 bp):
GAATTCCCGCCGCCACCATGGGCTGGTCCTGTATCATCCTGTTCCTGGTC

GCCACAGCCACCGGAGTGCACAGCGAGGTGCAGCTGGTGGAAAGCGGAGG

CGGCCTGGTTAAGCCCGGCGGATCTCTGAGACTGTCTTGTGCTGCCAGCG

GCTTCACCTTCAGCAACTTCGAGATGAACTGGGTGCGGCAGGCCCCTGGC

AAGGGACTGGAATGGGTCAGCGGCATCAGCTCTAATGGCAGATACATCAA

CTACGCCGACAGCGTGAAAGGCCGCTTCACAATCTCCAGAGATAACGCCA

AGAACAGCCTCTACCTGCAAATGAATAGCCTGCGGGCCGAGGACACCGCC

GTGTACTACTGCGCCAGAGTGGTGGACTTGACCAGGACTACAACGGCTTT

GATTATTGGGGCCAGGGCACACTGGTGACCGTGTCCAGCGCCAGCACCAA

GGGCCCCTCTGTCTTTCCTCTGGCCCCTTCTAGCAAATCTACAAGCGGAG

GCACCGCCGCCCTGGGTTGTCTGGTGAAAGACT

ACTTCCCAGAGCCTGTGACCGTGTCTTGGAACAGCGGCGCCCTGACCAGC

GGCGTGCACACATTCCCCGCTGTGCTGCAGAGCAGCGGCCTGTACAGCCT

GAGCAGCGTGGTCACCGTCCCCAGCAGCTCTCTGGGAACACAGACCTACA

TCTGCAACGTGAACCACAAGCCTTCTAATACCAAGGTGGATAAGAAGGTG

GAACCTAAGAGTTGCGACAAGACCCACACCTGTCCTCCGTGCCCCGCCCC

TGAGCTGCTGGGCGGCCCTAGCGTGTTTCTGTTCCCTCCAAAGCCCAAGG

ACACCCTGATGATCAGCAGAACCCCTGAGGTGACCTGCGTGGTGGTTGAT

GTGTCCCACGAAGATCCTGAGGTGAAGTTCAACTGGTACGTGGACGGCGT

TGAGGTGCATAATGCCAAGACAAAGCCAAGAGAGGAACAGTACAACAGCA

CATACAGAGTGGTGTCCGTGCTGACCGTGCTGCACCAGGACTGGCTGAAC

GGCAAAGAGTACAAGTGCAAGGTGTCCAACAAGG

CCCTGCCTGCTCCTATCGAGAAGACCATCAGCAAGGCTAAAGGACAGCCT

CGGGAACCCCAGGTCTACACCCTGCCCCCCAGCCGGGACGAGCTGACAAA

GAACCAGGTGTCCCTGACATGCCTGGTGAAGGGCTTCTACCCCTCCGACA

TCGCCGTGGAATGGGAGAGCAATGGCCAACCTGAAAACAACTACAAAACG

ACCCCTCCTGTTCTGGACAGCGACGGCAGCTTCTTCCTTTATAGCAAGCT

GACAGTGGACAAGAGCAGATGGCAGCAGGGCAACGTGTTCAGCTGCAGCG

TGATGCACGAGGCCCTCCACAACCACTACACCCAGAAGTCCCTGAGCCTG

TCTCCTGGCAAGTGATAAGCTT

SEQ ID NO: 3 CD179a IgG1/kappa construct
full-length light chain sequence (233 aa):
MGWSCIILFLVATATGVHSDIQLTQSPSFLSASVGDRVTITCRASQGIST

DLNWYQQKPGKAPKLLIYAASNLESGVPSRFSGSGSGTEFTLTISSLQPE

DFATYYCQQSYNWPYTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

SEQ ID NO: 4 CD179a IgG1/kappa construct
light chain nucleotide sequence (726 bp):
GAATTCCCGCCGCCACCATGGGCTGGTCCTGCATCATCCTGTTCCTGGTG

GCCACAGCCACCGGCGTGCACAGCGATATCCAGCTGACCCAGAGCCCCAG

CTTTCTGAGCGCCAGCGTGGGCGACCGGGTCACCATCACCTGTAGAGCCT

CTCAGGGCATCTCCACCGACCTCAACTGGTATCAGCAGAAACCTGGCAAG

GCCCCTAAGCTGCTGATCTACGCCGCTTCTAATCTGGAAAGCGGCGTGCC

ATCTAGATTCAGCGGCTCCGGCAGCGGCACCGAGTTCACCCTGACAATTA

GCAGCCTGCAGCCTGAGGACTTCGCCACATACTACTGCCAGCAAAGCTAC

AACTGGCCCTACACCTTCGGCGGAGGAACAAAGGTGGAAATCAAGAGAAC
```

```
-continued
CGTGGCCGCCCCTAGCGTGTTCATCTTCCCCCCCAGCGACGAGCAGCTGA

AGAGCGGTACAGCTTCTGTGGTGTGCCTGCTGAACAACTTCTACCCGCGG

GAAGCCAAGGTGCAGTGGAAGGTGGACAACGCCCTGCAGAGCGGCAACAG

CCAGGAGAGCGTGACAGAGCAGGACAGCAAGGACAGCACCTACAGCCTGA

GCAGCACCCTGACCCTGAGCAAGGCCGACTACGAGAAGCACAAGGTGTAC

GCCTGTGAAGTGACCCACCAGGGCCTGTCTAGCCCTGTGACCAAGTCTTT

TAACAGAGGCGAGTGCTGATAAGCTT
```

Antibody-Drug Conjugates (ADCs)

An important limitation for cell-based therapies against CD19, CD20, and CD22 immunotherapies in B-cell neoplasms is their elimination of all normal B cells that express these proteins on their cell surface; this leads to pan B-cell ablation with resultant immune dysregulation and immunocompromise. B-cell immunodeficiency after pan-B cell treatment ablates the patient's existing acquired immunity through vaccination and prior infections; it also temporarily removes the pool of naïve mature B-cells available to expand in response to new pathogenic challenges. This leads to considerable risk to the patient, since the exiting B-cell repertoires is critical to protect the patient from lifer-threatening infections.

Figure 13:
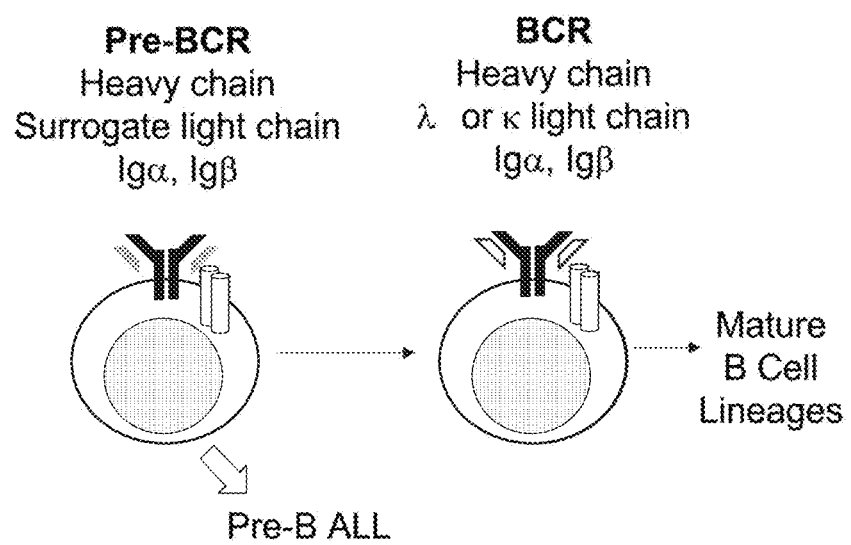
FIG. 13 shows a diagrammatic representation of the pre-BCR, comprised of a productively rearranged heavy chain, surrogate light chain components and the signaling chains, Igα and Igβ. In the mature BCR, the surrogate light chain is replaced with rearranged λ or κ light chain.

In humans, SLC expression is absent beyond B-cells that express IgM (Rolink, et al., 1991 *Cell* 66:1081-94; Winkler and Martensson, 2018 *Front Immunol* 9:2423). This difference is illustrated in FIG. 13, showing that precursor B cells express the pre-BCR distinguished by SLC (CD179) expression prior to rearrangement and expression of either the λ or κ light chains to comprise the mature BCR. Because the circulating CD179a-positive cell population represents only a small fraction (~1%) of the total B-cell pool, the effects of an antibody-drug conjugate (ADC) according to the disclosure is targeted towards the remaining B-ALL population and not the larger CD19-positive, antibody-producing B-cell repertoire. The resulting immunotherapy against the pre-BCR would spare a patient's mature B-cell repertoire, including the patient's existing antibody-producing B cells.

In one aspect, the disclosure provides an antibody-drug conjugate. In one embodiment, the ADC according to the disclosure is for use in the treatment of B-ALL. An antibody-drug conjugate (ADC) comprises a monoclonal antibody (mAb) conjugated to a cytotoxic payload via a chemical linker. By employing an antibody directed toward a target antigen expressed on a cell (for example, a cancer cell) surface, systemic exposure to the cytotoxic drug and the associated toxicity is reduced. Thus, normal tissue exposure is minimized, resulting in an improved therapeutic index and less damage to the surrounding, healthy tissue.

Monoclonal Antibody

In one embodiment, the monoclonal antibody of an ADC according to the disclosure is an anti-CD179a antibody. In another embodiment, the monoclonal antibody of an ADC according to the disclosure is IgG1 or IgG3. In still another embodiment, the monoclonal antibody of an ADC according to the disclosure is IgG1.

Cytotoxic Payload

The phrases "cytotoxic payload", "cytotoxic drug", and "cytotoxic agent" are used interchangeably herein. Cytotoxic drugs can be from natural sources or chemical synthesis. In certain embodiments, cytotoxic payload of an ADC according to the disclosure is selected based on potency, solubility, amenability to conjugation, and stability.

In certain embodiments, the cytotoxic payload is a clinically approved chemotherapeutic drug. In further embodiments, the chemotherapeutic agent is a biologically active anti-microtubule agent, an alkylating agent, or a DNA minor groove binding agent. Exemplary biologically active anti-microtubule agents include, but are not limited to, inhibitors of tubulin polymerization such as the maytansinoids (maytansine; DMs), dolastatins, auristatin drug analogs, and cryptophycin. Exemplary alkylating agents include, but are not limited to, duocarmycin derivatives such as CC-1065 analogs and duocarmycin. Exemplary agents that catalyze DNA double-strand breaks and agents that bind to the minor groove include, without limitation, enediyne antibiotics including esperamicin and calicheamicin and pyrrolobenzodiazepine (PBD).

In one embodiment, the cytotoxic payload of an ADC according to the disclosure is calicheamicin. Calechiamcin is a semi-synthetic derivative of N-acetyl $\Upsilon$-calicheamicin 1,2-dimethyl hydrazine dichloride (NAc $\Upsilon$-calicheamicin DMH). Calicheamicin is an antitumor antibiotic that binds to the minor groove of DNA in a sequence-specific manner (Hedrich, et al., 2018 *Clin Pharmacokinet* 57:687-703). This toxic payload has been used to effectively treat B-ALL in adults (Kantarjian, et al., 2016 *N Engl J Med* 375:740-53) and children (Bhojwani, et al., 2019 *Leukemia* 33:884-892). There are Phase 1 safety data in children for calicheamicin. Thus, an ADC in which the antibody is linked to calicheamicin becomes a targeted immunotherapeutic agent that responds to the above-mentioned continuing unmet need to create effective therapies for children, as called for by the FDA Reauthorization Act of 2017 (section V), and by the Best Pharmaceuticals for Children Act. This approach mitigates the significant lag-time that occurs in pediatric oncology trials that are dependent upon outcomes that must be first completed in adults.

Linker

In one embodiment, the linker of an ADC according to the disclosure is stable in circulation, but it releases the cytotoxic agent in the target cells. The linker can be cleavable or non-cleavable. Cleavable linkers, which respond to physiological stimuli such as low pH, high glutathione concentrations, and proteolytic cleavage, include, but are not limited to, chemically degradable linkers such as hydrazone and disulfide (SPP) and enzymatically degradable linkers such as Val-Cit-PABC and glucuronide-MABC. Non-cleavable linkers, which rely on degradation of the scaffold within the lysosome after internalization, include, but are not limited to, nondegradable alkyl and polymeric linkers such as maleimide alkane and maleimide cyclohexane (MCC). In one embodiment, the linker of an ADC according to the disclosure is an acid-labile 4-(4'-acetylphenoxy) butanoic acid (acetyl butyrate).

In certain embodiments, the antibody, linker, and payload of ADCs according to the disclosure are selected in order to optimize the safety and efficacy of the ADC. ADCs can generally be evaluated using techniques focusing on DAR (drug-to-antibody ratio) such as UV/vis spectroscopy and focusing on dispersity. In one embodiment, an antibody-drug conjugate according to the disclosure has a DAR between about 2:1 and about 10:1. In another embodiment, an antibody-drug conjugate according to the disclosure has a DAR between about 4:1 and about 6:1. In still another embodiment, an antibody-drug conjugate according to the disclosure has a DAR of about 5:1. ADCs can also be characterized employing hydrophobic interaction chromatography (HIC), standard reverse-phase high performance liquid chromatography (HPLC), MALDI-TOF, and ESI-MS, without limitation.

In certain embodiments, a CD179a antagonist for use in a method or pharmaceutical composition according to the invention is in the form of a calicheamicin-based antibody-drug conjugate (ADC) against CD179a.

In certain embodiments, ADCs according to the disclosure work against all genotypes represented within the B-ALL repertoire of molecular aberrations. No current B-ALL immunotherapies target autonomous survival signaling, which may be an important bypassing mechanism that leads to measurable resistant disease (MRD) and relapse.

Because of the comparative prevalence of B-lineage acute lymphoblastic leukemia in infants, children, and young adults and, by utilizing a calicheamicin-linked ADC, evaluation of the ADC disclosed herein may be expedited in Phase 1 testing, thus bringing the benefits of the novel agent into clinical use in children in need thereof. In additional embodiments, because of the highly-specific targeting of the B-ALL population, sparing normal CD19- or CD22-bearing B-cells, a lower relative dose of calicheamicin-linked ADC is used. Such reduction in dosing may have the additional benefit of reducing hepatotoxicity of the cytotoxic agent. In still further embodiments, the ADCs disclosed herein spare the adaptive immunity provided by the mature B-cell repertoire, including B-cells that produce antibodies that protect cancer patients from pathogens (Walton, et al., 2019 Pharmacoeconomics 37:1209-1217; Han, et al., 2018 *PLoS One* 13:e0191804). No current B-ALL immunotherapies are designed to preserve the protective effects of the antibody-producing mature B-cell repertoire.

Pharmaceutical Compositions

In one aspect, the present disclosure provides a pharmaceutical composition comprising a pre-BCR complex antagonist and one or more pharmaceutically acceptable vehicle, carriers, and/or excipients. In one embodiment, the antagonist is an antibody or antigen-binding fragment thereof that binds CD179a. In another aspect, the present disclosure provides a pharmaceutical composition comprising an antibody-drug conjugate and one or more pharmaceutically acceptable vehicle, carriers, and/or excipients. In one embodiment, the antibody is an antibody or antigen-binding fragment thereof that binds CD179a. Various pharmaceutically acceptable carriers and excipients are well-known in the art. See, e.g., Remington's Pharmaceutical Sciences, Mack Publishing Company, Easton, PA In some embodiments, the carrier is suitable for any contemplated mode of administration.

In one aspect, the present disclosure provides methods for treating B-ALL that comprise administering a pre-BCR complex antagonist to a subject, wherein the antagonist (e.g., an anti-CD179a antibody or antigen-binding fragment thereof) is contained within a pharmaceutical composition that comprises one or more pharmaceutically acceptable vehicle, carriers, and/or excipients. In another aspect, the present disclosure provides methods for treating B-ALL that comprise administering an antibody-drug-conjugate (ADC) to a subject, wherein the ADC is contained within a pharmaceutical composition that comprises one or more pharmaceutically acceptable vehicle, carriers, and/or excipients. In one embodiment, the antibody is an antibody or antigen-binding fragment thereof that binds CD179a.

Administration

In one embodiment, the pre-BCR complex antagonist, antibody-drug conjugate, or composition according to the disclosure is administered parenterally to a subject. In further embodiments, the pre-BCR complex antagonist, antibody-drug conjugate, or composition according to the disclosure can be administered to a subject intravenously or subcutaneously. In another embodiment, the pre-BCR complex antagonist, antibody-drug conjugate, or composition according to the disclosure can be administered to a subject via intravenous (IV) infusion. In one embodiment, the pre-BCR complex antagonist according to the disclosure is administered to a subject subcutaneously. In another embodiment, the antibody-drug conjugate according to the disclosure is administered to a subject via intravenous (IV) infusion. The infusion can be discrete or continuous. In another embodiment, the IV infusion occurs over a period of about 15 to about 300 minutes.

In certain embodiments, the pre-BCR complex antagonist, antibody-drug conjugate, or composition according to the disclosure can be administered to a subject once daily, once every 2 days, once every 3 days, once every 4 days, once every 5 days, once every 6 days, once weekly, once bi-weekly, once every 3 weeks, or once every 4 weeks. The frequency and duration of administration can be determined by a clinician based on primary and secondary endpoints evaluated in the subject. In certain embodiments, the endpoint is one or more of: reduction of disease burden in peripheral blood, reduction of disease burden in bone marrow, and/or reduction of disease burden in extramedullary sites, including pleural fluid, pericardial fluid, enlarged lymph nodes, liver, spleen, or any other body compartment outside the blood brain barrier.

Combination Therapies

In some embodiments, the pre-BCR complex antagonist, antibody-drug conjugate, or composition according to the disclosure is administered to a subject in combination with one or more additional therapies or therapeutic agents. "In combination" may mean sequentially (one after the other) or concurrently (at the same time). In further embodiments, the additional therapy or therapeutic agent is any chemotherapeutic agent, cytokine, or medication designed to reduce tumor burden. In still further embodiments, the additional therapy or therapeutic agent is a supportive care agent, for example, an anti-emetic agent, a blood products, resuscitative fluid, or some other intervention required for patient care.

In certain embodiments, the combination therapy or agent may be reduced in dosage or frequency because of the efficacy of the antagonist/ADC/composition administered to the subject.

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. The IgG1 Anti-VpreB1 mAb is Highly-Specific to the Pro- and Pre-B Stages of B-ALL To assess the surface expression of CD179a in B-ALL, annotated clinical data were used to include NCI Risk status, cytogenetic features, and end-Induction MRD levels of ≥1% to select 36 diagnostic cases from COG Biology Study AALL03B1 (NCT00482352): 11 from Standard Risk AALL0331 (NCT00103285) and 25 from High Risk AALL0232 (NCT00103285) (FIG. 1). Of the 36 cases evaluated, 32 were arrested at the CD10-positive pre-B stage (some also expressive of CD20) and four at the CD10-negative pro-B stage.

To determine whether CD179a continued to be expressed following a month-long course of induction therapy, 16 paired Day 28 samples were obtained for further testing, seven from AALL0331 and nine from AALL0232. All subjects and/or their legally-authorized representatives provided written, informed consent in accordance with the Declaration of Helsinki. The laboratory study protocols were approved by the COG Cell Bank (AALL18B2-Q), the NIH Cancer Therapeutics Evaluation Program, and by the Children's Minnesota IRB.

Diagnostic and end-Induction B-lymphoblast populations were assessed using 6-color flow cytometry as previously described (Borowitz, et al., 2015 *Blood* 126:964-71). Samples were stained with two different 6-color antibody combinations (CD20-FITC/CD10-PE/CD38-PerCPCy5.5/CD58-APC/CD19-PECy7/CD45-APCH7 and CD9/CD13+33/CD34/CD10/CD19/CD45), including a third tube with SYTO-16 to identify all nucleated cells and a commercially-available, PE-conjugated CD179a (Biolegend, San Diego, CA). In cases where a paired, Day 28 sample was available, and/or there were sufficient viable cells for further sorting, a fourth tube was included to test a recombinant FITC-conjugated mAb against CD179a (Erasmus, et al., 2016 *Science Signaling* 9) (produced by GenScript, Piscataway, NJ); FITC-labeling of the mAb was performed in accordance with the manufacturer's instructions (Abcam, Cambridge, MA). Unlike the FITC-labeled conjugate, the PE-labeled conjugate does not undergo internalization (Erasmus, et al., 2016). CD3-PerCP, CD10-PE, CD13+/33-APC, and CD19-PeCy7 were used as protocol controls; positive and negative controls for the FITC-conjugated CD179a mAb were tested against Nalm6 cells (FIGS. 4A-4D). All analyses were performed on a Becton-Dickinson FACSCanto™ II 6-color cell analyzer in a CLIA/CAP certified laboratory. Cases with ≥20% CD179a surface expression were determined to be positive for chi-squared analyses; all comparisons were performed using Graphpad Prism 8.6 software (San Diego, CA).

Results

Relapsed or progressive disease in B-ALL may arise from a pervasive genetic/epigenetic reprogramming of B-lymphoblasts in what has been termed "senescence-associated stemness (SAS)" (Milanovic, et al., 2018 *Nature* 553:96-100). Because these changes are not reversed with the cessation of induction chemotherapy, relapse-initiating B-lymphoblasts exit SAS and establish therapy-resistant cell populations (identifiable as MRD), which then undergo clonal expansion, leading to relapse and death. These phenomena are especially common in KMT2A-Rs, BCR/ABL1, and other high-risk molecular lesions. In cases where autonomous signaling through the pre-BCR results in a therapy-resistant population, there is an opportunity to specifically kill the relapse-initiating pool, regardless of genotype.

Using gene expression profiling analyses, it has previously been reported that pre-BCR+ ALL comprised a minor subset of B-ALL cases, most of which harbored TCF3/BPBX1, KMT2A-R and other cytogenetic findings (Kohrer, et al., 2016 *Leukemia* 30:1246-54). Thirty-four cases arrested at the CD10-positive pre-B stage were evaluated herein, as were two cases at the CD10-negative pro-B stage (FIG. 2A). The molecular genotype table shown in FIG. 2A documents the relative expression of the control and experimental anti-CD179a (VpreB1) mAbs in the 36 B-ALL samples.

Using the VpreB-PE and the VpreB-FITC mAbs, 36 diagnostic cases were tested for VpreB surface expression in Day 0 cryopreserved samples that were obtained from children and young adults with NCI standard and high-risk B-ALL. Cases were subdivided into pro-B and pre-B ALL based upon the absence or presence of co-expression with CD10 and CD20. There was no correlative difference in VpreB expression for pro-B (CD10 negative), or pre-B ALL (CD10 positive, either CD20 negative or positive) (FIGS. 3A and 3B; P=NS, one-way ANOVA). Indeed, no statistical differences in VpreB expression were found among three developmental stages of B-ALL arrest, but all cases except four showed >20% expression using either the PE-conjugated or the FITC-conjugated CD179a mAbs. Lack of VpreB expression could not be correlated with the presence or absence of any recurring molecular aberrations shown in the molecular genotype table.

In Day 0 diagnostic sample, VpreB-PE expression ranged from 0% to 95.2% (55.3±3.9%), and for the FITC-conjugated mAb, expression ranged from 14% to 46.7% (mean 29.6±2.1%) (FIG. 4A, 4B; unpaired t-test, P<0.001).

One or both mAbs showed that CD179a was present in ≥20% of the B-lymphoblast population, ranging from 20.2% to 90.6% for all 36 diagnostic samples, including three cases for which RNA-seq data were available for comparative analyses (FIG. 2B) (Gu, et al., 2019 *Nat Genet* 51(2):296-307). The Heavy Chain Re-Arrangement Table of FIG. 2B shows the PAPDNB, PAEYT, and PAPNWH cases that were tested for pre-BCR IgH chain components, all of which were re-arranged (see column for Symbol) and in all cases had undergone re-arrangement of the heavy chain. These three components were normalized against a cohort of 630 B-ALL cases, showing that there is molecular evidence that the heavy chain had undergone re-arrangement in the cases that were studied. This is significant, as the pre-BCR complex only traffics to the cell surface if the heavy chain is productively re-arranged and expressed concurrently with the two surrogate light chain components, CD179a and b. Compared to gene expression-based predictions for the incidence of pre-BCR+ALL, anticipated to be ~16%, a significant difference was found between expected versus observed flow-based CD179a positivity—every case expressed CD179a in the series of 36 (two-sided Fisher's exact test, P<0.001). This establishes that B-ALL patients will be broadly eligible for anti-PreBCR treatment.

Similar to previous findings, CD179a expression was observed in cases having E2A-PBX3, KMT2A-R; however, CD179a expression was additionally found in other cases, but also with BCR-ABL1, with phenotypic features that are sometimes expressed by mixed phenotype acute leukemias (MPALs (Arber, et al., 2016 *Blood* 127:2391-2405), and in other genotypes that may present with ambiguous lineages. Because CD179a was ubiquitously expressed in the series of 36 cases, it is likely broadly targetable in B-ALL, including cases with elevated end-induction MRD, and regardless of genotype, stage of developmental arrest, NCI risk status, or molecular aberrations. Moreover, this genotype-independent receptor ligand was expressed in cases with no known molecular targets or curative therapies (e.g., TCF3-HLF, Pt #22), indicating that immunotherapeutic targets against CD179a may provide therapeutic options across a broad spectrum of B-ALL subtypes.

Figure 5A:
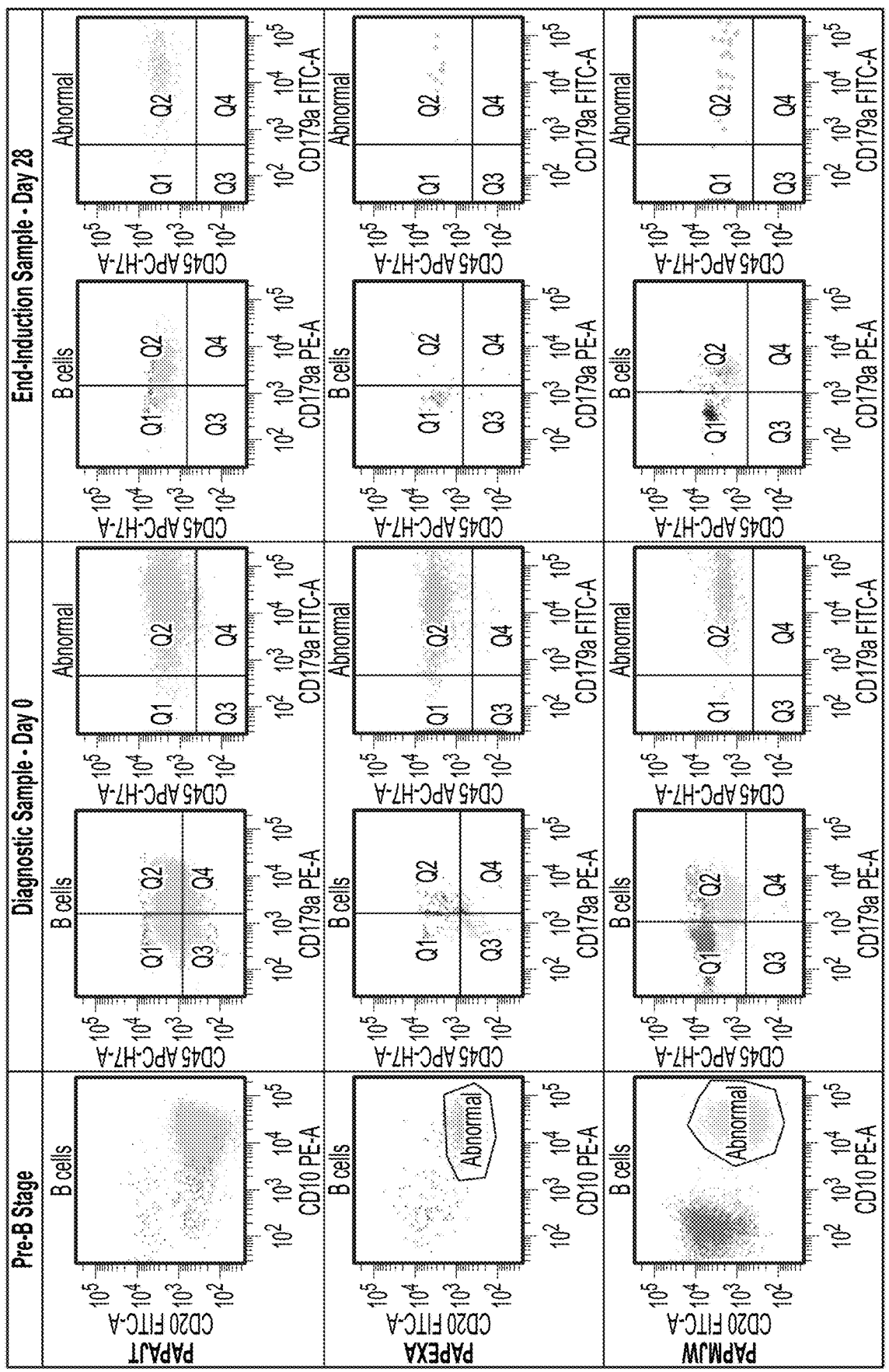

Since transient dimerization via the SLC is responsible for governing self-autonomous signaling in early B-cells, it was hypothesized that the abnormal MRD population might escape apoptotic cell death following induction chemotherapy (Table 1, below). Using two CD179a-specific mAbs, embedded in the COG MRD Panel, both mAbs were found to identify pre-BCR expression in an abnormal B-cell population, as identified by the COG MRD Panel (FIGS. 4C, 4D). For the PE-conjugated mAb, Day 29 expression ranged from 0.4% to 69.9%, (mean 18.4±5.9%), and for the FITC-conjugated mAb, expression ranged from 2.0% to 68.1% (mean 33.4±5.2%) (P=0.07) (FIG. 5A). The monoclonal antibody was able to be conjugated to the FITC fluorochrome (FIG. 5B), supporting the antibody's identification of B-ALL. PE and FITC photon spectral intensities differ, the former fluorochrome having brighter emission with laser excitation at 488 nm. Variations in detectable pre-BCR expression between the two anti-CD179a mAbs may be attributable to several phenomena, including differences between mAb specificity and sensitivity, differential sensitivities in N-glycosylation on the IgH N46 SLC association site in recovering marrow samples (Ubelhart, et al., 2010 *Nat Immunol* 11:759-65). The CD179a-FITC mAb showed greater detectable expression in the end-induction samples than the CD179a-PE mAb, indicating that the mAb may have an enhanced sensitivity/affinity to B-lymphoblasts that co-mingle with an expanding pool of hematogones, which may also be present in a recovering marrow. (Kurzer, et al., 2018 *J Clin Pathol* 71:845-850; Rimsza, et al. 2000 *Am J Clin Pathol* 114(1):66-75; Rimsza, et al., 1998 *Am J Clin Pathol* 110(3):313-320). Two different antibodies against CD179a were utilized, to gain deeper insight into the ligand's expression and suitability for clinical targeting. Taken together, these results show that the eligible population is broader than expected from the leukemia literature and not informed by prior art in this area.

TABLE 1

Day 28 samples and Induction chemotherapy regimens

| Study (subjects) | Day 28 Samples Induction Chemotherapy Regimens | | | |
|---|---|---|---|---|
| | vincristine | pegaspargase | daunorubicin | dexamethasone |
| AALL0331 (7) | D 1, 8, 15, 22 | D 4 or 5 or 6 | Not given | D 1-28 |
| AALL0232 (9) | D 1, 8, 15, 22 | D 4 or 5 or 6 | D 1, 8, 15, 22 | D 1-14 |

Thus, an anti-CD179a antibody as described herein detects ligand on B lineage leukemia cells. The ligand may be responsible for mediating minimum residual disease (MRD).

Because CD19, CD20, CD22 (and less commonly, CD38) are ubiquitously expressed in B-cell neoplasms, these surface receptors are targets for cell-based therapies (Hunger and Mullighan, 2015 *N Engl J Med* 373:1541-52; Bonifant and Tasian, 2020 *Curr Opin Pediatr* 32:13-25). Trials utilizing rituximab, an anti-CD20 mAb, have been successful, but were limited in accrual and subsequent implementation in clinical practice by the rarity of CD20 expression in B-ALL (Bonifant and Tasian). As described above, an important limitation for use of anti-CD19, CD20, and CD22 immunotherapies in the treatment of B-ALL is the unfortunate outcome of eliminating all normal (non-leukemic) mature B cells, which leads to pan B-cell ablation and immune dysregulation. Immunotherapy based upon anti-pre-BCR antibodies may spare the patient's existing mature B cell repertoire. Extending the results described herein towards safer, more effective outcomes in cancer therapy underscores the importance of considering novel cell-based targets, including CD179a, for future clinical trials in B-ALL.

Example 2. A Calicheamicin-Based Antibody-Drug Conjugate (ADC) Against CD179a is Tested and Shows Efficacy in Human B-ALL Cell Lines and PDX Lines A first-in-class, novel ADC against the VpreB1 component of the pre-BCR was developed. The ADC was designed to spare the adaptive immunity provided by the mature B-cell repertoire, thus precluding the need for long-term supportive care and avoiding the cytokine release with imbalanced T-cell activation that results from other therapies.

Figure 6:
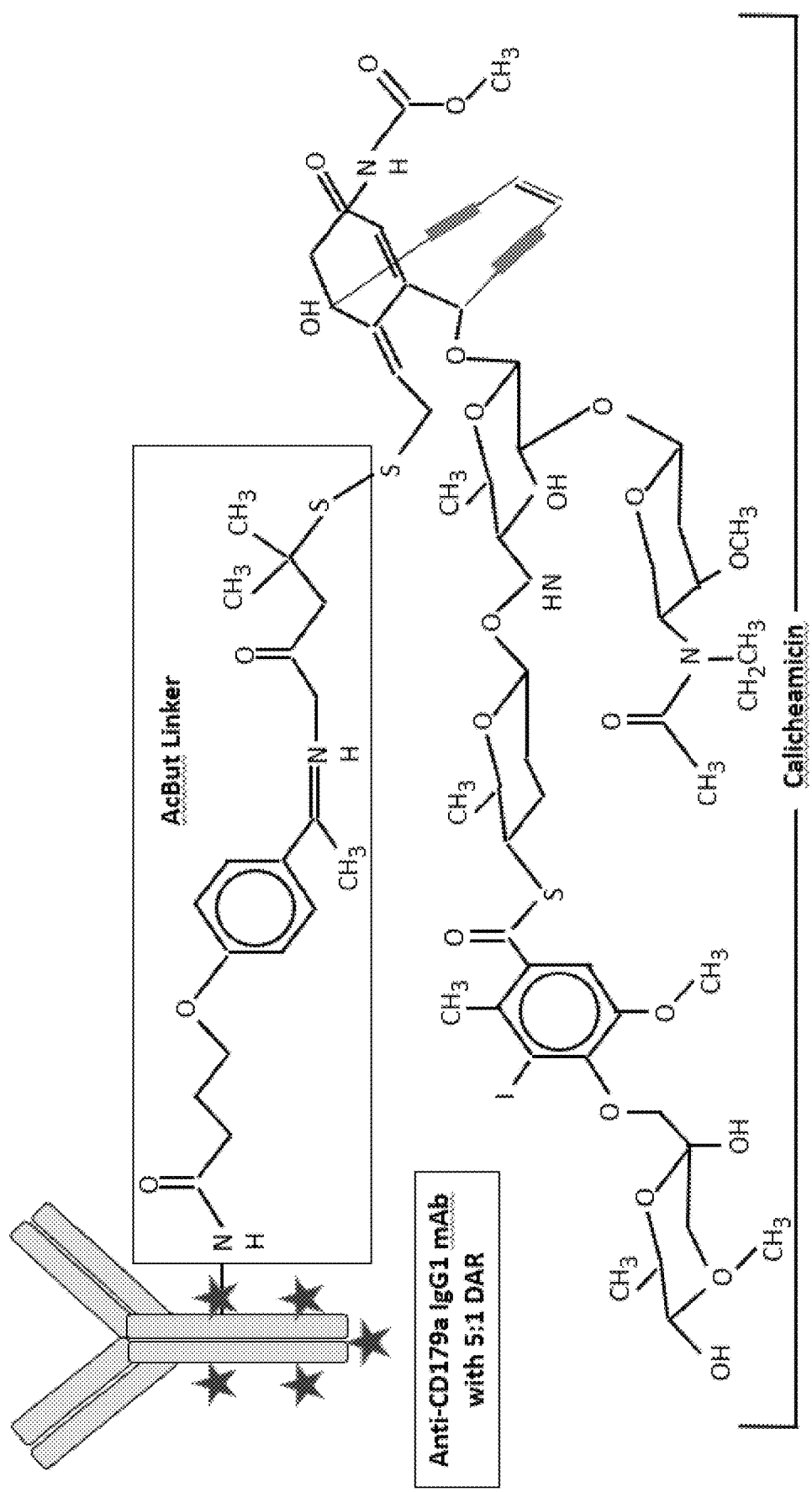
FIG. 6 shows a diagram of the calicheamicin-based antibody-drug conjugate (ADC) against CD179a, including an AcBut linker.
Figure 7A:
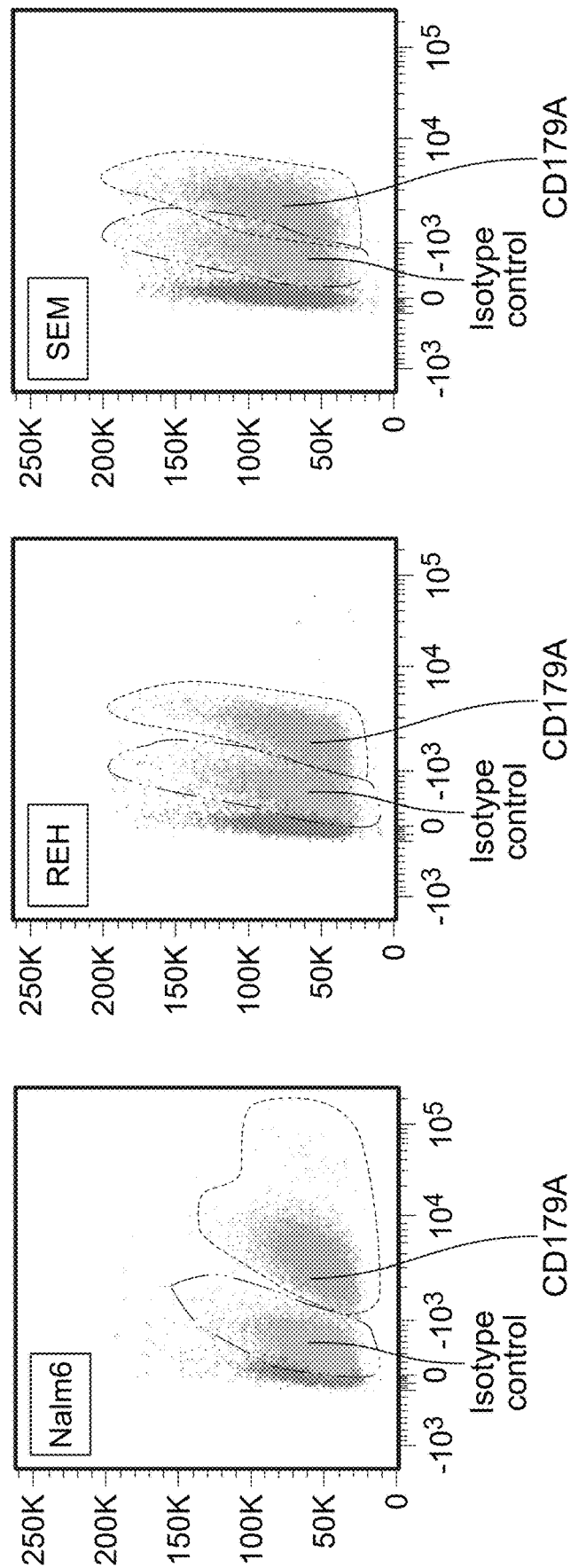

A monoclonal antibody that specifically binds CD179a was linked to calicheamicin as payload to develop the ADC.
Human IgG1 Antibody Preparation According to the amino acid sequence information of the human IgG1 antibody, the nucleic acid sequences were optimized based on the eukaryotic expression system, and expression vectors were constructed. The expression vectors of the antibody were transiently transfected and expressed in HEK293 cells with chemically defined culture media. The mAb was purified by Protein A affinity chromatography, size-exclusion chromatography, endotoxin removal, ultrafiltration, and then subjected to 0.2-micron sterile filtration to get the bulk of high purity.
AcBut-Calicheamicin Preparation AcBut-Calicheamicin was prepared as linker-payload. The structure of AcBut-Calicheamicin is shown in FIG. 6. FIG. 6 shows a diagram of the antibody-drug conjugate (ADC). The conjugates were analyzed via HIC and SEC Chromatography, showing that the Calicheamicin was conjugated to the antibody successfully, and that the ADC product was stable with low un-conjugated Ab percent and no obvious aggregation. The endotoxin level was acceptably low. EC50s indicated that the ADCs exhibited comparable (antigen) binding activity to control antibody. The ADC prepared herein exhibited a DAR of 5:1.
CD179a Expression The expression of the antigen, CD179a, was evaluated in various cell lines (B-ALL cell lines Nalm6, REH, SEM and B-ALL PDX cell lines PDX B1, PDX B2) (FIGS. 7A and 7B). A fluorochrome-tagged naked antibody was used to track expression. CD179a was found to be highly expressed in B-lineage cell lines.
Cell Proliferation/Viability Assessment In order to determine whether the pre-BCR can be decoupled from autonomous survival signaling by a targeted ADC, and in an effort to prevent resistant disease states that are induced by cancer treatments, the calicheamicin-linked anti-Vpreb1 mAb ADC against the B-ALL was tested in a series of existing B-ALL models.

Figure 8A:
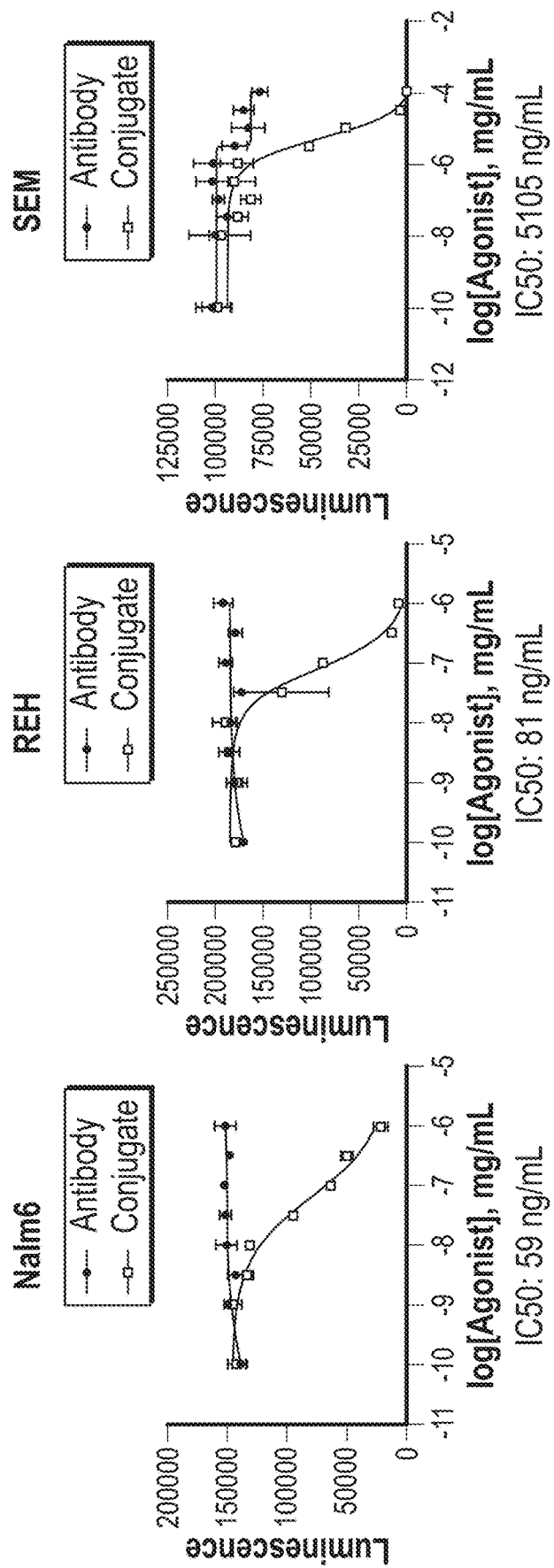
FIGS. 8A and 8B show the cell proliferation/viability assessed in various B-lineage cell lines (FIG. 8A: B-ALL cell lines Nalm6, REH, SEM and FIG. 8B:B-ALL PDX cell lines PDX B1, PDX B2) at 48 hours post-treatment with the ADC (for Nalm6, REH, SEM) and 24 hours post-treatment with the ADC (for PDX B1, PDX B2).
Figure 8B:
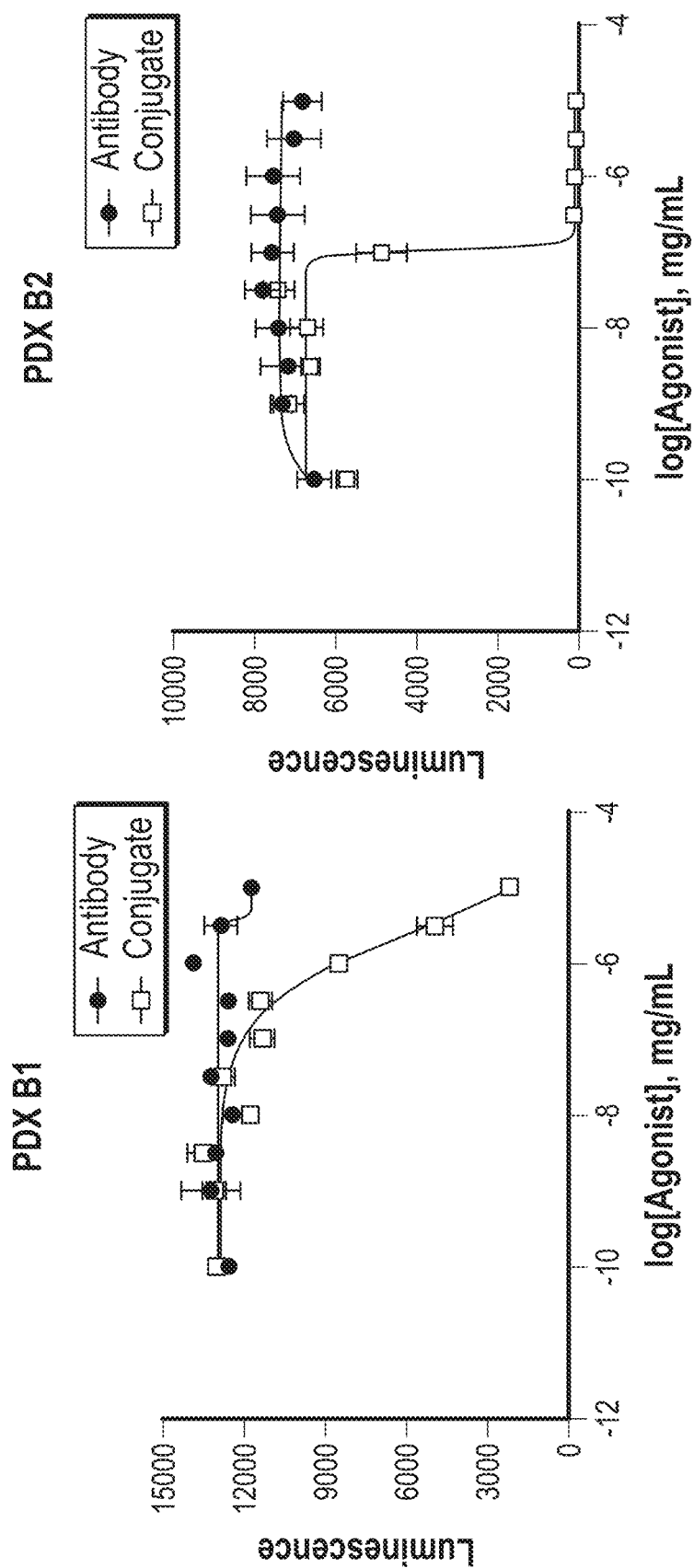

Cell proliferation/viability was assessed in the cell lines (B-ALL cell lines Nalm6, REH, SEM and B-ALL PDX cell lines PDX B1, PDX B2) at 48 hours post-treatment with the ADC (for Nalm6, REH, SEM) and 24 hours post-treatment with the ADC (for PDX B1, PDX B2) (FIGS. 8A and 8B). The graphs show the B-ALL cell death as a result of treatment with the ADC. Furthermore, IC50 values are provided for each graph, where the IC50=the inhibitory concentration that causes 50% pf cells to die.

Because the pre-BCR complex rapidly internalizes upon binding, the naked antibody served as the negative control for the experiments. Antibodies that internalize would not be expected to utilize antibody-dependent cellular cytotoxicity or antibody-dependent cellular phagocytosis (ADCC/ADCP) as mechanisms of action.

Apoptosis Measurement

Figure 9A:
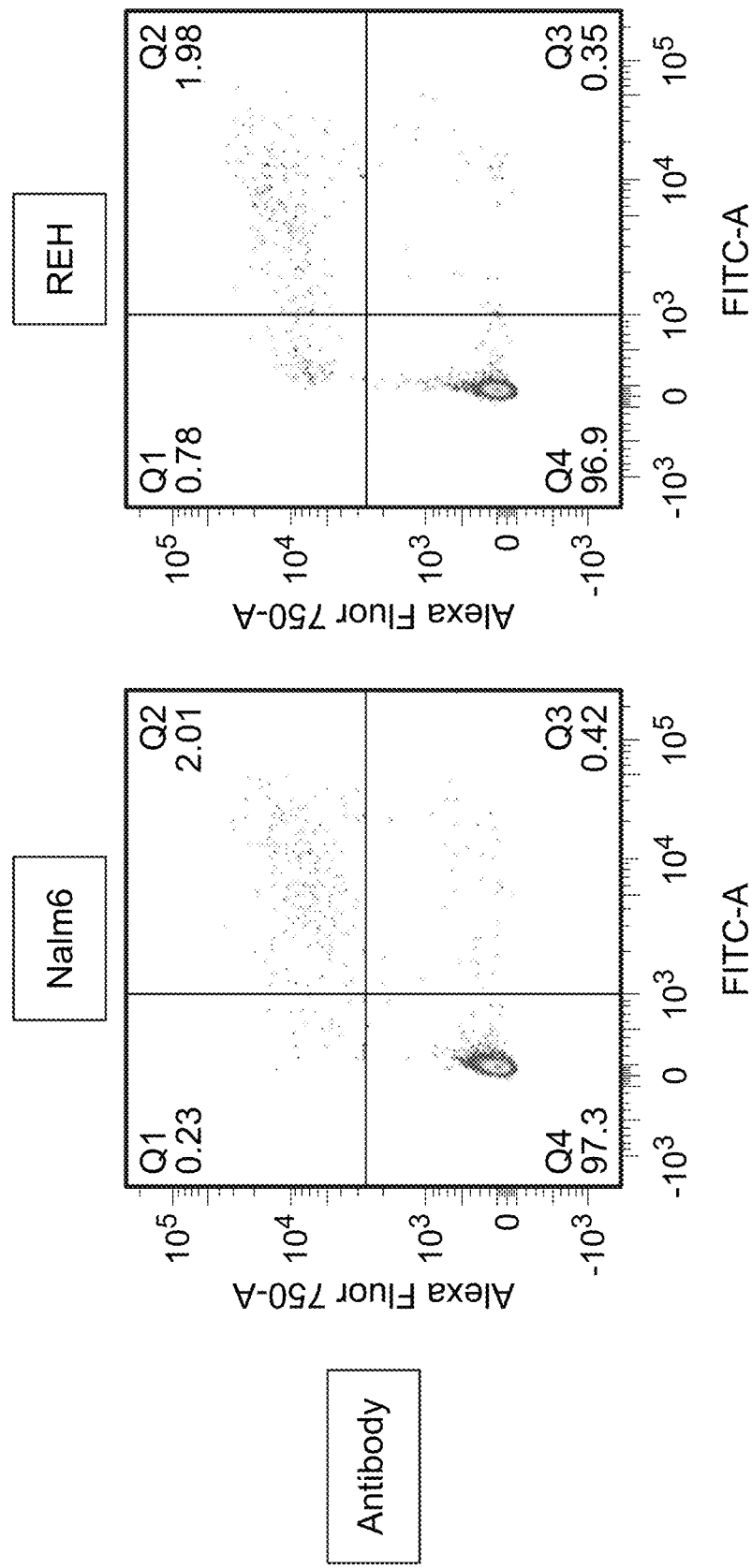

Because Cell-titer-glo reagent is a better measure of proliferation than cell viability, apoptosis in B-lineage cell lines treated with the ADC was measured by annexin-V (early apoptosis; x-axis FIGS. 9A and 9B) and cell live/dead stain (late apoptosis; y-axis FIGS. 9A and 9B). The flow histograms shown in FIG. 9B show significant cell death by apoptosis in the right upper quadrant for the Nalm6 and REH cells treated with the ADC. In comparison, the flow histograms shown in FIG. 9A show little apoptosis in the same cells treated with antibody alone.

Example 3. A Calicheamicin-Based Antibody-Drug Conjugate (ADC) Against CD179a is Tested and Shows Efficacy in an NSG Mouse (NOD Scid Gamma Mouse) Model NSG immunocompromised mice engrafted with human leukemia cells are useful models for initial evaluation of targeted therapies. Here, NSG mice were exposed to two control conditions and one experimental condition. Briefly, 6 animals in each test group were given phosphate buffered saline ("mock" treated—"control" in FIG. 10), naked antibody (not expected to utilize ADCC/ADCP mechanisms of action—"CD179A Ab" in FIG. 10), or the antibody-drug-conjugate (ADC—"CD179A Ab-drug" in FIG. 10). All animals were inoculated via tail vein ion with the human Nalm6 B-ALL cell line (IC50=59 ng/mL) at the outset of the experiment (and would typically succumb to disease after about three weeks of incubation time). Treatment (control and experimental intervention) began when peripheral leukemia cells were detected by flow cytometry. Treatment consisted of 3 mg/kg/dose ADC intraperitoneally administered every 4 days for 3 total doses. All animal studies were approved under category "D" by an IACUC-certified animal facility. Time elapsed was measured in days, and the probability of survival was calculated by the Kaplan-Meier method.

Figure 10:
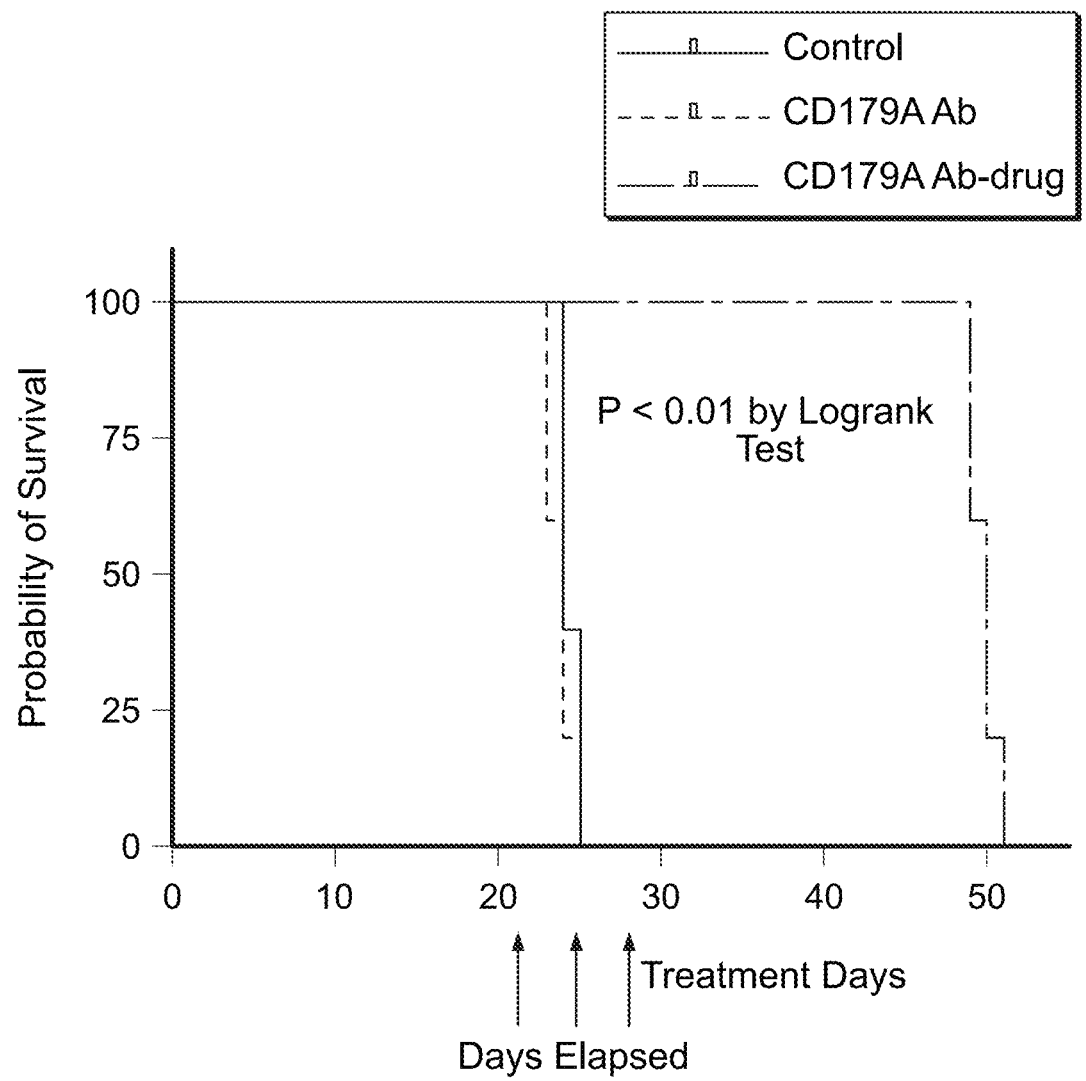
FIG. 10 shows the survival of mice (treated with PBS, antibody alone, and ADC) over time.
Figure 11:
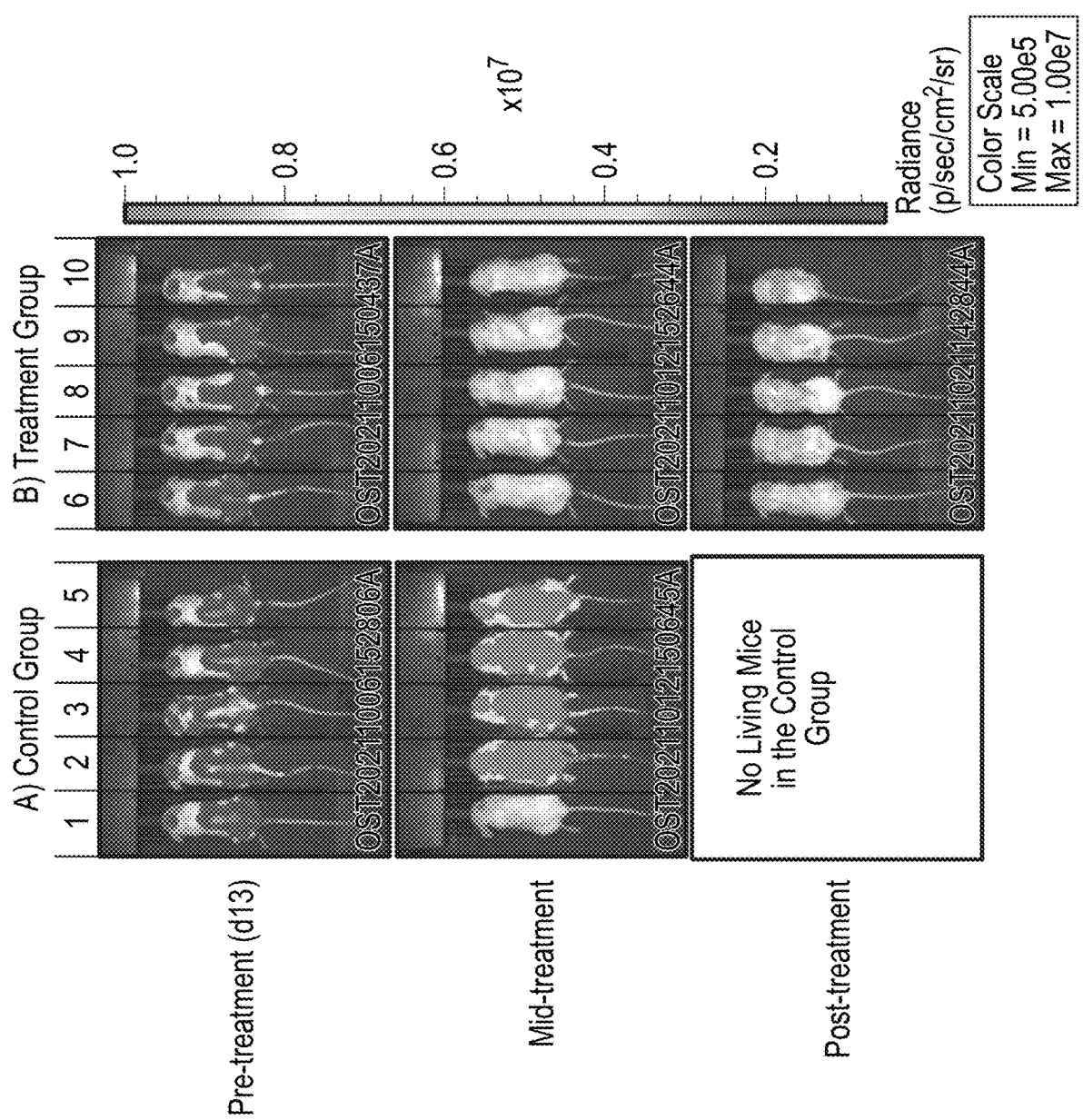
FIG. 11 shows progression-free survival in ADC-untreated and treated NSG mice. Panel A (left): "Control Group" bioluminescence data for 5 NSG mice that underwent tail vein injection with Nalm6-bioluminscent B-lineage lymphoblasts and were mock-treated with intraperitoneal injections of phosphate buffered saline, 3 doses, 4 days apart at days. At mid-treatment, four of five mice (lanes 2-5) showed advanced leukemic progression. The mouse in lane 1 was moribund at the time of imaging and appears white due to its impaired perfusion. Panel B (right): "Treatment Group" bioluminescence data for 5 NSG mice that underwent tail vein injection with Nalm6-bioluminscent B-lineage lymphoblasts and were treated with intraperitoneal injections of the ADC, with doses at 3 mg/kg, 4 days apart. The bioluminescent data show that all of the animals in the ADC-treated group (lanes 6-10) achieved remission from the Nalm6 cell line, as measured by bioluminescence.

FIG. 10 shows that while the mice treated with PBS or antibody alone did not survive past three weeks, the mice treated with the ADC survived to day 40. In these pre-clinical experiments in NOD.Cg-Prkdcscidll2rgtm1jl/SzJ (NSG) mice that were co-cultured with B-ALL cell line Nalm6, mouse survival time was essentially doubled when compared to mock-treated mice, or those treated with naked antibody. FIG. 11 shows bioluminescence data for 10 animals, five that were mock treated and five with the ADC (3 mg/kg given intraperitoneally, 3 doses, 4 days apart). The data show that all of the animals in the ADC-treated group achieved a remission, as measured by bioluminescence. The mock-treated control group animals showed a high leukemia burden, in comparison. These results show that the calicheamicin-linked ADC is an effective agent in treating B-ALL in the NSG experimental model.

In a follow-up experiment, four of six animals in the Treatment Group showed no evidence of disease by necropsy when euthanized three weeks after the completion of the treatment phase (data not shown).

Figure 12:
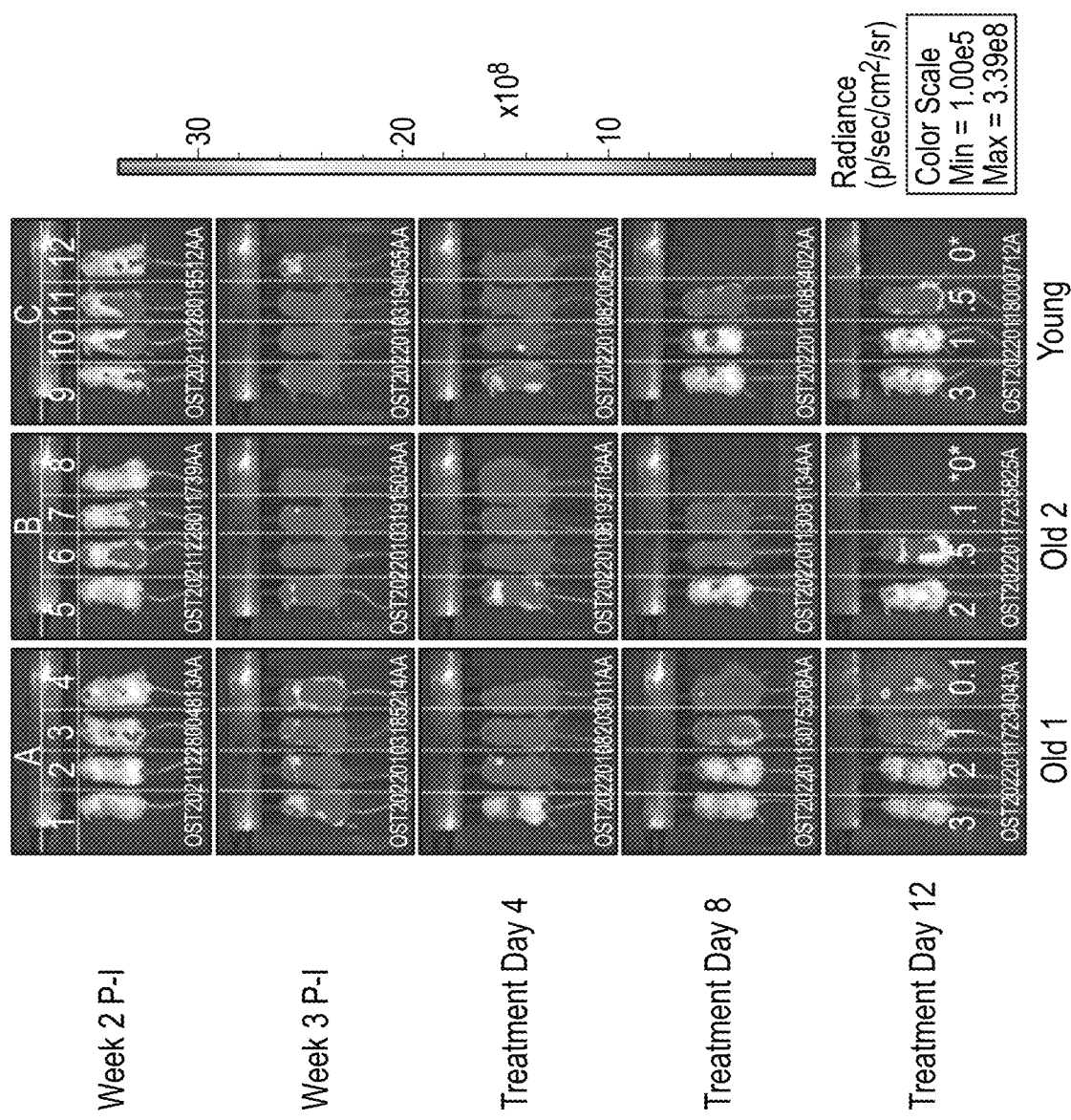
FIG. 12 shows bioluminescence data for all animals at Weeks 2 and 3 pre-intraperitoneal injection (Week 2 P-I and Week 3 P-I) and after Treatment Days 4, 8 and 12. The Control conditions ("0") consisted of intraperitoneal injections of phosphate buffered saline. Panel A, left (Lanes 1-4), shows that in older NSB mice treated with 2 mg/kg and 3 mg/kg of the ADC, disease progression was prevented and reversed. Panel B, middle (lanes 5-8), shows that disease progression was reversed in older NSG mice at a dose of 2 mg/kg. Disease progression was attenuated with a dose of 0.5 mg/kg. Panel C right (Lanes 9-12), shows that disease progression could be reversed in younger NSG mice treated in doses from 1 to 3 mg/kg.

Next, dose-finding studies using the NSG murine platform were carried out. Dose titrations for the ADC in concentrations ranged from 0.1, 0.5, 1, 2 and 3 mg/kg in 4 NSG mice each treated with 3 doses, 4 days apart. After allowing the Nalm6-bioluminescence to reach a pre-morbid level, the animals were give 3 doses each, separated by four days. Bioluminescence data were collected for all animals throughout the course of the experiment, which consisted of imaging studies at Weeks 2 and 3 pre-intraperitoneal injection (Week 2 P-I and Week 3 P-I) and after Treatment Days 4, 8 and 12. Taken together, the data (FIG. 12) show that doses of 2 mg/kg may be sufficient to induce remission, but not in doses less than 0.5 mg/kg.

Because it appears that doses of 2 mg/kg are as effective as 3 mg/kg (had similar clearance of leukemia burden), a lower dose of the ADC may be justified in the settings of pediatric and adult clinical trials. This dosing strategy additionally allows the reduction of the exposure of calicheamicin from 160 mcg/kg to approximately 120 mcg/kg, with the potential added benefit of reducing the occurrence of calicheamicin-induced hepatotoxicity.

Thus, using a calicheamicin-conjugated mAb against the VpreB1 component of the pre-BCR, a novel therapeutic agent is developed herein that is highly specific to B-lineage acute lymphoblastic leukemia (B-ALL). Based upon the concurrent protection of the patient's existing mature B cell adaptive immunity, the novel ADC disclosed herein was designed to be safer and more effective than other ADCs in its class.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A pharmaceutical composition comprising an antibody-drug conjugate (ADC), wherein the antibody or an antigen-binding fragment thereof specifically binds CD179a, and a pharmaceutically acceptable carrier, wherein the antibody or antigen-binding fragment thereof that specifically binds CD179a comprises three heavy chain complementarity determining regions, HCDR1, HCDR2, and HCDR3 having the amino acid sequences of SEQ ID NOs: 7, 8, and 9, respectively, and three light chain complementarity determining regions, LCDR1, LCDR2, and LCDR3 having the amino acid sequences of SEQ ID NOs: 10, 11, and 12, respectively, wherein the antibody or antigen-binding fragment thereof that specifically binds CD179a comprises a heavy chain comprising an amino acid sequence having at least 95%, at least 96%, at least 97%, at least 98%, or at least 99% sequence identity with the amino acid sequence of SEQ ID NO:1 and a light chain comprising an amino acid sequence having at least 95%, at least 96%, at least 97%, at least 98%, or at least 99% sequence identity with the amino acid sequence of SEQ ID NO:3, wherein the drug is calicheamicin, and wherein the pharmaceutical composition is for use in the treatment of B-cell acute lymphoblastic leukemia (B-ALL) or B lymphoblastic lymphoma.

2. The pharmaceutical composition of claim 1, wherein the antibody or antigen-binding fragment thereof that specifically binds CD179a comprises a heavy chain comprising the amino acid sequence of SEQ ID NO: 1 and a light chain comprising the amino acid sequence of SEQ ID NO:3.

3. The pharmaceutical composition of claim 1, wherein the ADC binds B lineage leukemia cells.

4. The pharmaceutical composition of claim 1, wherein the ADC does not bind normal mature B cells.

5. The pharmaceutical composition of claim 1, wherein the antibody or antigen-binding fragment thereof is conjugated to the drug by an acetyl butyrate linker.

6. A method for treating B-cell acute lymphoblastic leukemia (B-ALL) or B lymphoblastic lymphoma in a subject, comprising administering to the subject the pharmaceutical composition of claim 1.

7. The method of claim 6, wherein the antibody that specifically binds CD179a comprises a heavy chain comprising the amino acid sequence of SEQ ID NO: 1 and a light chain comprising the amino acid sequence of SEQ ID NO:3.

8. The method of claim 6, wherein the ADC binds B lineage leukemia cells.

9. The method of claim 6, wherein the ADC does not bind normal mature B cells.

10. The method of claim 6, wherein the subject is human.

11. The method of claim 10, wherein the subject is adult.

12. The method of claim 10, wherein the subject is pediatric.

13. The method of claim 6, wherein the composition is administered intravenously to the subject.

* * * * *